United States Patent [19]

Franz et al.

[11] 4,187,099

[45] Feb. 5, 1980

[54] 3-ARYL-4-ISOTHIAZOLECARBOXYLIC ACID AND 3-ARYL-4-ISOXAZOLECARBOXYLIC ACID DERIVATIVES AND THEIR USE AS HERBICIDES

[75] Inventors: John E. Franz, Crestwood; Robert K. Howe, Bridgeton, both of Mo.

[73] Assignee: Monsanto Company, St. Louis, Mo.

[21] Appl. No.: 852,164

[22] Filed: Nov. 16, 1977

[51] Int. Cl.$^2$ ............................................. A01N 9/12
[52] U.S. Cl. ........................................... 71/90; 71/88
[58] Field of Search ............................................. 71/90

[56] References Cited

U.S. PATENT DOCUMENTS

| | | | |
|---|---|---|---|
| 3,155,678 | 11/1964 | Hatchard | 260/302 |
| 3,699,115 | 10/1972 | Franz | 260/302 A |

OTHER PUBLICATIONS

Howe et al., Jr. Chem. Soc. Chem. Comm., (1973), pp. 524–525.
Franz et al., Tetrahedron Letters, No. 16, (1970), pp. 1381–1384.

*Primary Examiner*—Catherine L. Mills
*Attorney, Agent, or Firm*—Richard H. Shear; Donald W. Peterson

[57] ABSTRACT

Carboxylic acid derivatives having the formula

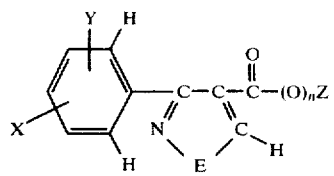

have been found to be effective herbicides. They are especially effective when applied as a pre-emergent herbicide.

7 Claims, No Drawings

3-ARYL-4-ISOTHIAZOLECARBOXYLIC ACID AND 3-ARYL-4-ISOXAZOLECARBOXYLIC ACID DERIVATIVES AND THEIR USE AS HERBICIDES

The invention relates to the use of 3-aryl-4-isothiazolecarboxylic acid derivatives and 3-aryl-4-isoxazolecarboxylic acid derivatives as herbicides.

The carboxylates may be represented by the formula

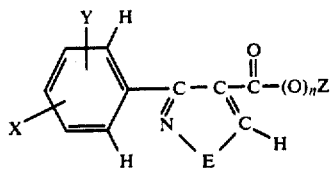
(I)

wherein E is oxygen or sulfur; X and Y are independently selected from the group consisting of hydrogen, lower alkyl, lower alkoxy, trifluoromethyl, halogen, cyano and nitro; n is zero or one provided that when n is zero, Z is selected from the group consisting of chloro and $NR_1R_2$ wherein $R_1$ and $R_2$ are independently selected from the group consisting of hydrogen and lower alkyl; when n is one, Z is selected from the group consisting of alkyl having up to 12 carbon atoms inclusive, haloalkyl, benzyl, lower alkoxy lower alkyl, allyl, monochlorinated allyl, dichlorinated allyl,

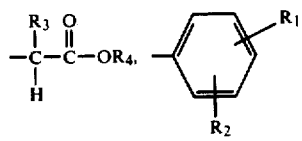

and agriculturally acceptable cations; wherein $R_1$ and $R_2$ are as previously defined, $R_3$ is hydrogen or methyl and $R_4$ is lower alkyl.

As used herein, the term "lower alkyl" and "lower alkoxy" is understood to include those alkyl and alkoxy groups having up to 5 carbon atoms, inclusive. The term "haloalkyl" is understood to mean those lower alkyl groups which have been substituted with from 1 to 3 halogen atoms, inclusive. The term "agriculturally acceptable cations" is understood to mean those cations that are commonly used to form the salt of the free acid. Such cations include, but are not limited to, alkali metal, alkaline earth, substituted amine and ammonium cations. The term "alkyl" includes primary, secondary and tertiary alkyls.

The carboxylic acid derivatives of the foregoing formula have been found to be rather effective in inhibiting the growth of undesirable weeds, especially when applied in what is known in the art as a pre-emergent treatment. This is somewhat surprising in view of U.S. Pat. No. 3,403,209 wherein isothiazole carboxylates are disclosed to be fungicidal having very low phytotoxicity.

The compounds may be prepared utilizing a number of different procedures. The first procedure summarized below as Scheme A illustrates the preparation of 3-aryl-4-isothiazolecarboxylic acid esters.

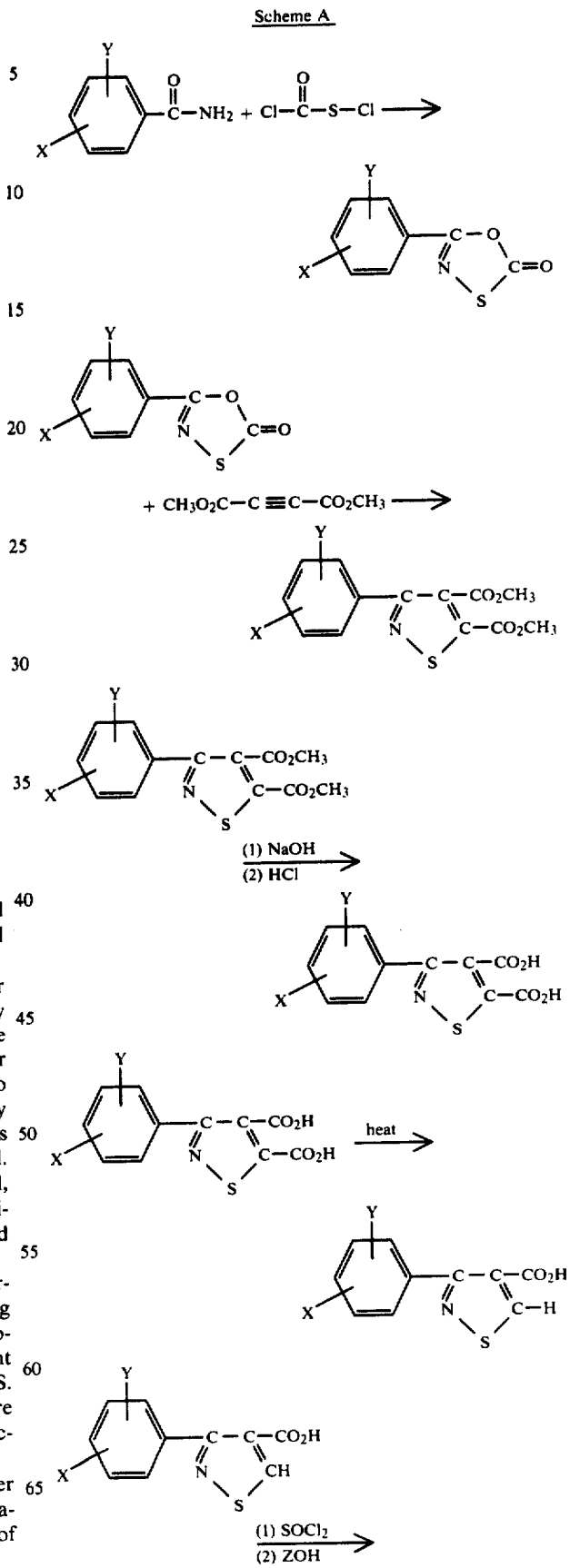

-continued
Scheme A

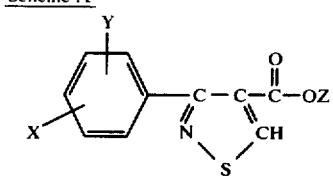

In accordance with Scheme A, 1.25–1.50 equivalents of chlorocarbonylsulfenyl chloride prepared in accordance with British Pat. No. 1,079,348 is dissolved in a suitable solvent, such as toluene, along with the appropriate benzamide. The solution is stirred and heated at approximately 100° C. until gas evolution has nearly ceased and/or until an infrared spectrum has revealed the absence of residual amide. Up to 5.0 equivalents of chlorocarbonylsulfenyl chloride can be employed with less reactive amides. Concentration of the reaction mixture under vacuum and crystallization of the residue from an appropriate solvent results in a 5-aryl-1,3,4-oxathiazol-2-one.

A solution of 0.10 moles of the oxathiazolone and 0.20 moles of dimethyl acetylenedicarboxylate in 60 ml of an appropriate solvent, such as chlorobenzene, is stirred at reflux until CO2 evolution ceases. After removal of the solvent and the excess dimethyl acetylenedicarboxylate, the dimethyl 4,5-isothiazoledicarboxylate is crystallized from an appropriate solvent.

The dicarboxylate is then hydrolyzed by first treating the dimethyl 4,5-isothiazoledicarboxylate with an excess of sodium hydroxide in water. For very insoluble esters, a small amount of dioxane may be added to the reaction mixture. The resultant solution may then be acidified to a pH of less than 1.0 with an excess of concentrated hydrochloric acid and then extracted several times with ether. The ether layers are combined, dried (CaSO4), and concentrated under vacuum.

Monodecarboxylation of the 4,5-isothiazoledicarboxylic acids may then be effected by heating said acid in an appropriate solvent, such as o-dichlorobenzene at reflux. The solution is then allowed to cool and the solid product collected, washed and recrystallized.

Esters of the isothiazole-4-carboxylic acid may then be obtained by heating said acid with an excess of thionyl chloride at reflux. The resultant solution is concentrated under vacuum and heated at reflux with the appropriate alcohol. The solution may then be concentrated to give pure ester or in the case of solids, the solid may then be recrystallized.

In order to illustrate the preparation of 3-aryl-4-isothiazolecarboxylates by the methods of Scheme A, the following examples are presented.

All examples presented herein are only for purposes of illustration and are not intended as a limitation in the scope of the invention. All temperatures are understood to be Centigrade.

5-Aryl-1,3,4-oxathiazol-2-ones may be prepared in accordance with Examples 1–5.

EXAMPLE 1

Preparation of 5-Phenyl-1,3,4-Oxathiazol-2-One, Chlorocarbonylsulfenyl chloride was prepared by a literature procedure. A mixture of 784.9 g (4.22 mol) of trichloromethanesulfenyl chloride and 76 g (4.22 mol) of water dissolved in 886 ml of concentrated H2SO4 was stirred at 45°–50° for 1 hour in a 5 l. flask, at which time the initially-copious HCl evolution had ceased. (Foaming presented problems in the beginning.) The mixture was transferred to a separatory funnel, and after 15 minutes, the layers were separated. The top, fluid layer, which amounted to 404.3 g (3.08 mol, 73% yield) of fairly pure chlorocarbonylsulfenyl chloride, was added to 373 g (3.08 mol) of benzamide in 1 l. of toluene in a 5 l. flask fitted with stirrer and reflux condenser. The mixture was stirred vigorously and was heated gently to 58°. A mildly exothermic reaction carried the temperature to 65° with foaming and vigorous gas evolution. The mixture was heated at 65° for 20 minutes, at 70° for 8 hours, at 70°–110° for 0.5 hours, and at 110° for 0.75 hours, at which time gas evolution had ceased. The reaction mixture was concentrated under vacuum to 1.5 mm and 90°. The residue was heated with 650 ml of methylcyclohexane; the mixture was treated with charcoal, filtered, and allowed to cool. The resultant solid was recrystallized from 650 ml of methylcyclohexane, heated to 75° (charcoal treatment and filtration) to give 375 g of very pale yellow solid, 5-phenyl-1,3,4-oxathiazol-2-one, m.p. 64°–67°. An additional 27.2 g of product, m.p. 64°–67°, was obtained from the filtrates. The total yield, 412.2 g, corresponds to 75% of the theoretical amount.

EXAMPLE 2

Preparation of 5-(m-Tolyl)-1,3,4-Oxathiazol-2-One m-Toluamide (116 g, 0.86 mol) and chlorocarbonylsulfenyl chloride (144 g, 1.1 mol, 28% excess) was heated to 100° C. in 400 ml of toluene, with stirring, for 5.5 hours. Cooling resulted in an orange solid. The solid, isolated by filtration, was dissolved in hot methylcyclohexane and decolorized. The light yellow product was recrystallized once from methylcyclohexane to give 76.05 g (45.8%) of white solid, m.p. 82.5°–84°.

Anal. Calc'd. for $C_9H_7NO_2S$: C, 55.94; H, 3.65. Found: C, 56.07; H, 3.59.

EXAMPLE 3

Preparation of 5-(m-Chlorophenyl)-1,3,4-Oxathiazol-2-One. m-Chlorobenzamide (75 g, 0.48 mol) and chlorocarbonylsulfenyl chloride (79 g, 0.6 mol, 25% excess) were reacted as described in Example 2 for 1.5 hours. Volatile components were removed under reduced pressure. The dark brown oil was taken up in hot cyclohexane, and the mixture was filtered. Cooling resulted in separation of a dark orange solid. The solid, recrystallized twice from hot ethyl acetate, gave 64.21 g (0.316 mol, 65.8%) of off-white solid, m.p. 83°–84.5°.

Anal. Calc'd. for $C_8H_4ClNO_2S$: C, 44.97; H, 1.89. Found: C, 44.92; H, 1.62.

EXAMPLE 4

Preparation of 5-(α,α,α-Trifluoro-m-Tolyl)-1,3,4-Oxathiazol-2-One. α,α,α-Trifluoro-m-toluamide (82.7 g, 0.437 mol) and chlorocarbonylsulfenyl chloride (86 g, 0.667 mol, 53% excess) were reacted under the conditions of Example 2 for 0.5 hours. The light yellow residue was dissolved in ethyl acetate and cooled to −78°. The white precipitate was filtered and washed with hexane to yield 93.14 g (0.377 mol, 86.2%) of white solid, m.p. 85°–86.5°.

Anal. Calc'd. for $C_9H_4F_3NO_2S$: C, 4.373; H, 1.63. Found: C, 43.66; H, 1.58.

EXAMPLE 5

Preparation of 5-(α,α,α,α',α',α'-Hexafluoro-3,5-Xylyl)-1,3,4-Oxathiazol-2-One. 3,5-Bis(trifluoromethyl)benzamide (60.5 g, 0.235 mol) and five equivalents of chlorocarbonylsulfenyl chloride (154 g, 1.175 mol) were heated in 600 ml of toluene at reflux, with stirring, for 12 hours. The crude product, a dark brown oil, weighed 77.5 g. After decolorization in hexane, the material was taken up in methanol and recrystallized three times to give 22.0 g (0.0699 mol, 29.75%) of pale gold solid, m.p. 61°–62.5°.

Anal. Calc'd. for $C_{10}H_3F_6NO_2S$: C, 38.11; H, 0.96. Found: C, 38.22; H, 0.90.

Additionally, the following compounds may be prepared in accordance with Examples 1–5.

5-(3',4'-dimethoxyphenyl)-1,3,4-oxathiazol-2-one, m.p. 143°–144.5°.

5-(3',4'-dichlorophenyl)-1,3,4-oxathiazol-2-one, m.p. 130.5°–131.5°.

5-(p-cyanophenyl)-1,3,4-oxathiazol-2-one, m.p. 173° with decomposition.

5-(p-nitrophenyl)-1,3,4-oxathiazol-2-one, m.p. 168°–169° with decomposition.

5-(p-chlorophenyl)-1,3,4-oxathiazol-2-one, m.p. 129°–131°.

5-(m-nitrophenyl)-1,3,4-oxathiazol-2-one, m.p. 95°–96.5°.

The dicarboxylate may be prepared in accordance with Examples 6–13.

EXAMPLE 6

Preparation of Dimethyl 3-Phenyl-4,5-Isothiazoledicarboxylate. A solution of 412.2 g (2.3 mol) of 5-phenyl-1,3,4-oxathiazol-2-one, 662.7 g (4.66 mol) of dimethyl acetylenedicarboxylate, and 1 l. of chlorobenzene was heated at 135° for 6.5 hours, at which time $CO_2$ evolution became very slow. Infrared and gas chromatography assays also indicated that the reaction was complete. The reaction mixture was concentrated under vacuum to 0.2 mm and 90°. The 680 g of pot residue was crystallized from about 700 ml of methanol to give 393 g of solid dimethyl 3-phenyl-4,5-isothiazoledicarboxylate, m.p. 70°–71.5°. An additional 69.9 g of solid, m.p. 70°–72°, was obtained from the filtrate. The total of 462.9 g amounted to a 72.7% yield.

EXAMPLE 7

Preparation of Dimethyl 3-(α,α,α,α',α',α'-Hexafluoro-3,5-Xylyl)-4,5-Isothiazoledicarboxylate. A solution of 20.7 g (0.0657 mol) of 5-(α,α,α,α',α',α'-hexafluoro-3,5-xylyl)-1,3,4-oxathiazol-2-one and 18.7 g (0.131 mol) of dimethyl acetylenedicarboxylate in 52 g of o-dichlorobenzene was held at reflux for 10 hours (gas chromatography assay revealed the product had formed in 77% yield) and was concentrated under vacuum to 90° at 0.5 torr. The residue was crystallized from methanol to give 17.9 g of solid, m.p. 71°–74°. The solid was recrystallized to give 14.3 g (53% yield) of white solid, m.p. 73°–75°.

Anal. Calc'd. for $C_{15}H_9F_6NO_4S$: C, 43.59; H, 2.19. Found: C, 43.77; H, 2.13.

EXAMPLE 8

Preparation of Dimethyl 3-(3,4-Dimethoxyphenyl)-4,5-Isothiazoledicarboxylate. 5-(3,4-Dimethoxyphenyl)-1,3,4-oxathiazol-2-one (58 g, 0.24 mol) and dimethyl acetylenedicarboxylate (70 g, 0.49 mol) were heated at reflux in 120 ml of chlorobenzene for 43 hours. The residue crystallized from methanol at −29°, was recrystallized once from methanol, twice from ethyl acetate, and twice from methylcyclohexane to yield 59.07 g (0.175 mol, 73.0%) of pale yellow solid, m.p. 113.5°–11.45°.

Anal. Calc'd. for $C_{15}H_{15}NO_6S$: C, 53.41; H, 4.48. Found: C, 53.03; H, 4.46.

EXAMPLE 9

Preparation of Dimethyl 3-(3,4-Dichlorophenyl)-4,5-Isothiazoledicarboxylate. 5-(3,4-Dichlorophenyl)-1,3,4-oxathiazol-2-one (99.2 g, 0.4 mol) and dimethyl acetylenedicarboxylate (113.5 g, 0.8 mol) were heated in 240 ml of chlorobenzene at reflux for 47 hours. The product, from hot methanol, was recrystallized twice from hot methanol to give 97.8 g (0.283 mol, 70.7%) of white solid, m.p. 105°–107°.

Anal. Calc'd. for $C_{13}H_9Cl_2NO_4S$: C, 45.10; H, 2.62. Found: C, 45.12; H, 2.58.

EXAMPLE 10

Preparation of Dimethyl 3-(p-Cyanophenyl)-4,5-Isothiazoledicarboxylate. Dimethyl acetylenedicarboxylate (42.63 g, 0.4 mol) and 5-(p-cyanophenyl)-1,3,4-oxathiazol-2-one (20.42 g, 0.1 mol) were heated at reflux in o-dichlorobenzene for 10 hours. Volatile materials were removed under reduced pressure (1 mm). The red-brown residue contained at least three contaminants (g.c.) which were removed by crystallization from methanol. Four recrystallizations resulted in 18.1 g (0.0598 mol, 59.8%) of light yellow solid, m.p. 134°–135°.

Anal. Calc'd. for $C_{14}H_{10}N_2O_4S$: C, 55.62; H, 3.33. Found: C, 55.55; H, 3.23.

EXAMPLE 11

Preparation of Dimethyl 3-(p-Nitrophenyl)-4,5-Isothiazoledicarboxylate. Dimethyl acetylenedicarboxylate (85.26 g, 0.6 mol) and 5-(p-nitrophenyl)-1,3,4-oxathiazol-2-one (33.63 g, 0.15 mol) were heated as given above for 15 hours. Crystallization of the brown solid from methanol (2X) gave little improvement in purity. The brown solid was decolorized in ethyl acetate solution and recrystallized (3X) to give 12.2 g (0.0378 mol, 25.2%) of dark gold solid, m.p. 142°–143°.

Anal. Calc'd. for $C_{13}H_{10}N_2O_6S$: C, 48.45; H, 3.13. Found: C, 48.76; H, 3.18.

EXAMPLE 12

Preparation of Dimethyl 3-(m-Tolyl)-4,5-Isothiazoledicarboxylate. 5-m-Tolyl-1,3,4-oxathiazol-2-one (19.32 g, 0.1 mol) and dimethyl acetylenedicarboxylate (28.42 g, 0.2 mol) were heated at reflux in 60 ml of chlorobenzene as given above. After the initial crystallization from cold methanol, three recrystallizations from diethyl ether/petroleum ether gave 15.18 g (0.0522 mol, 52.2%) of white solid, m.p. 53°–54.5°.

Anal. Calc'd. for $C_{14}H_{13}NO_4S$: C, 57.72; H, 4.50. Found: C, 57.79; H, 4.20.

EXAMPLE 13

Preparation of Dimethyl 3-(m-Chlorophenyl)-4,5-Isothiazoledicarboxylate. 5-(m-Chlorophenyl)-1,3,4-oxathiazol-2-one (21.37 g, 0.1 mol) and dimethyl acetylenedicarboxylate (28.42 g, 0.2 mol) were heated in 60 ml of chlorobenzene at reflux as above for 32 hours. After crystallization once from methanol and twice from diethyl ether/petroleum ether, 16.11 g (0.0517 mol, 51.7%) of the pale yellow solid was obtained, m.p. 69°–70°.

Anal. Calc'd. for $C_{13}H_{10}ClNO_4S$: C, 50.09; H, 3.23. Found: C, 50.25; H, 3.42.

Hydrolysis of the dicarboxylate is illustrated by Examples 14–19.

EXAMPLE 14

Preparation of 3-($\alpha,\alpha,\alpha,\alpha',\alpha',\alpha'$-Hexafluoro-3,5-Xylyl)-4,5-Isothiazoledicarboxylic Acid. A mixture of 14.7 g (0.0356 mol) of dimethyl 3-($\alpha,\alpha,\alpha,\alpha',\alpha',\alpha'$-hexafluoro-3,5-xylyl)-4,5-isothiazoledicarboxylate, 7.2 g (0.18 mol) of NaOH, and 45 ml of water was held at reflux for 2 hours, was cooled, extracted twice with ether, and acidified with 30 ml (0.36 mol) of concentrated HCl. The resultant mixture was extracted three times with ether; these ether extracts were combined, dried (CaSO$_4$), and concentrated under vacuum to 12.8 g (93.4%) of white solid, m.p. 193°–193.5° with decomposition.

Anal. Calc'd. for $C_{13}H_5F_6NO_4S$: C, 40.53; H, 1.31. Found: C, 40.31; H, 1.18.

EXAMPLE 15

Preparation of 3-(3,4-Dimethoxyphenyl)-4,5-Isothiazoledicarboxylic Acid. The diester was hydrolyzed with five equivalents of NaOH in aqueous dioxane at reflux for 3 hours. The mixture was cooled, acidified with concentrated HCl, and extracted several times with ether (total volume=3 l.) and with 1.5 l. of 1:1 ether-THF. The organic layers were combined, dried (CaSO$_4$), and concentrated to give 45.06 g of crude product. A sample was recrystallized twice from 90% aqueous ethanol to give a hydrated product, m.p. 190.5°–191.5° with decomposition (fast), m.p. 216°–217° with decomposition (slow; monoacid).

Anal. Calc'd. for $C_{13}H_{11}NO_6S \cdot 0.7\ H_2O$: C, 48.50; H, 3.88. Found: C, 48.73; H, 4.10.

EXAMPLE 16

Preparation of 3-(3,4-Dichlorophenyl)-4,5-Isothiazoledicarboxylic Acid. A mixture of 51.9 g (0.15 mol) of dimethyl 3-(3,4-dichlorophenyl)-4,5-isothiazoledicarboxylate and 30 g (0.75 mol) of NaOH in 150 ml of water was held at reflux for 2 hours, was cooled, acidified with HCl, and was extracted with ether several times (total ether volume equals 1300 ml). The ether solution was dried (CaSO$_4$) and concentrated to give 46.12 g of solid. A small sample was recrystallized twice from water and once from ether-dichloroethane to give pure product, m.p. 187.5°–188.5° with decomposition (fast).

Anal. Calc'd. for $C_{11}H_5Cl_2NO_4S$: C, 41.53; H, 1.58. Found: C, 41.56; H, 1.60.

EXAMPLE 17

Preparation of 3-(m-Tolyl)-4,5-Isothiazoledicarboxylic Acid. Dimethyl 3-(m-tolyl)-4,5-isothiazoledicarboxylate (14.03 g, 0.0548 mol) was hydrolyzed in NaOH (10.96 g, 0.274 mol) and 50 ml H$_2$O for 0.5 hours at reflux. Acidification with HCl, extraction with ether and recrystallization gave a light yellow solid, m.p. 166.5°–167° with decomposition.

Anal. Calc'd. for $C_{12}H_9NO_4S$: C, 54.75; H, 3.45. Found: C, 54.54; H, 3.63.

EXAMPLE 18

Preparation of 3-(m-Chlorophenyl)-b 4,5-Isothiazoledicarboxylic Acid. Dimethyl 3-(m-chlorophenyl)-4,5-isothiazoledicarboxylate (14.51 g, 0.0504 mol) was hydrolyzed as given above with NaOH (10.08 g, 0.252 mol) and then acidified with HCl. The purified yellow solid had m.p. 185°–6° with decomposition (rapid heating of the sample produced normal decomposition in this temperature range; slow heating caused a color change to red and m.p. 217.5°–218.5° with decomposition. Infrared of material heated slowly to 190° showed that it was 3-(m-chlorophenyl)-4-isothiazolecarboxylic acid).

Anal. Calc'd. for $C_{11}H_6ClNO_4S$: C, 46.57; H, 2.13. Found: C, 46.50; H, 2.17.

EXAMPLE 19

Preparation of 3-(p-Chlorophenyl)-4,5-Isothiazoledicarboxylic Acid. Dimethyl 3-(p-chlorophenyl)-4,5-isothiazoledicarboxylate (35.0 g, 0.112 mol) was hydrolyzed in NaOH (22.6 g, 0.56 mol) was stated above. Acidification with HCl and the usual workup as in Example 14 gave a purified pale yellow solid which had m.p. 177°–177.5° with decomposition.

Anal. Calc'd. for $C_{11}H_6ClNO_4S$: C, 46.57; H, 2.13. Found: C, 46.22; H, 2.26.

Decarboxylation of the dicarboxylic acids is illustrated by Examples 20–25.

EXAMPLE 20

Preparation of 3-(m-Tolyl)-4-Isothiazolecarboxylic Acid. 3-(m-Tolyl)-4,5-isothiazoledicarboxylic acid (7.98 g, 0.0303 mol) was heated in 25 ml of o-dichlorobenzene at vigorous reflux for 15 minutes and cooled. Hexane was added and the resultant precipitate was filtered off to yield 5.52 g (0.0258 mol, 83.1%) of a light pink solid, m.p. 144.5°–146°.

Anal. Calc'd. for $C_{11}H_9NO_2S$: C, 60.26; H, 4.14. Found: C, 60.21; H, 4.04.

EXAMPLE 21

Preparation of 3-(m-Chlorophenyl)-4-Isothiazolecarboxylic Acid. 3-(m-Chlorophenyl)-4,5-isothiazledicarboxylic acid (8.0 g, 0.0282 mol) was reacted as previously stated. The dark tan solid was crystallized from ethylene chloride/acetonitrile solution to give 5.84 g (0.0244 mol, 86.6%) of white solid, m.p. 215°–216°.

Anal. Calc'd. for $C_{10}H_6ClNO_2S$: C, 50.11; H, 2.52. Found: C, 50.32; H, 2.47.

EXAMPLE 22

Preparation of 3-(p-Chlorophenyl)-4-Isothiazolecarboxylic Acid. 3-(p-Chlorophenyl)-4,5-isothiazoledicarboxylic acid recrystallization residues were heated at reflux as given above for 0.5 hours. On cooling a tan precipitate formed which was crystallized from acetonitrile and from ethylene chloride to yield a white solid having m.p. 181.5°–182.5°.

EXAMPLE 23

Preparation of 3-($\alpha,\alpha,\alpha,\alpha',\alpha',\alpha'$-Hexafluoro-3,5-Xylyl)-4-Isothiazolecarboxylic Acid. A solution of 11.7 g of diacid in 100 ml of o-dichlorobenzene and 30 ml of ether was heated on a hot plate, and the ether was allowed to distill off. The solution was allowed to boil at 180° for 10 minutes, was cooled, and was filtered to give a solid. This material was recrystallized from heptane to give 5.52 g of white solid, m.p. 152°–154°.

Anal. Calc'd. for $C_{12}H_5F_6NO_2S$: C, 42.24; H, 1.48. Found: C, 42.13; H, 1.34.

An additional 3.14 g of solid, m.p. 151°–153.5° was obtained by concentration of the o-dichlorobenzene filtrate and crystallization of the residue once from heptane and once from 1,2-dichloroethane.

EXAMPLE 24

Preparation of 3-(3,4-Dimethoxyphenyl)-4-Isothiazolecarboxylic Acid. A 42 g sample of diacid was heated in 100 ml of nitrobenzene at reflux for 15 minutes. The solution was cooled, diluted with 150 ml of hexane, and filtered. The resultant solid was crystallized twice from dioxane and once from 85% aqueous ethanol to give 32.6 g (90%) of solid, m.p. 215.5°–216° with decomposition.

Anal. Calc'd for $C_{12}H_{11}NO_4S.0.2\ H_2O$: C, 53.60; H, 4.27. Found: C, 53.63; H, 4.20.

A small sample was recrystallized twice from ethyl acetate and dried at 80° (<0.1 torr).

Anal. Calc'd. for $C_{12}H_{11}NO_4S$: C, 54.33; H, 4.18. Found: C, 54.32; H, 4.24.

EXAMPLE 25

Preparation of 3-(3,4-Dichlorophenyl)-4-Isothiazolecarboxylic Acid. A 19.1 g sample of diacid was heated in o-dichlorobenzene at reflux for 15 minutes. Cyclohexane was added to the cooled mixture, and the resultant 14.41 g of solid was recrystallized from 90% aqueous ethanol and from ethertoluene to give pure product, m.p. 247°–247.5° with decomposition.

Anal. Calc'd. for $C_{10}H_5Cl_2NO_2S$: C, 43.82; H, 1.84. Found: C, 43.84; H, 1.87.

Examples 26–45 illustrate the esterification of 3-aryl-4-isothiazolecarboxylic acid by preparing the acid chloride with thionyl chloride and reacting said acid chloride with the appropriate alcohol.

EXAMPLE 26

Preparation of Methyl 3-($\alpha,\alpha,\alpha,\alpha',\alpha',\alpha'$-Hexafluoro-3,5-Xylyl)-4-Isothiazolecarboxylate. A solution of 7.50 g (0.022 mol) of 3-($\alpha,\alpha,\alpha,\alpha',\alpha',\alpha'$-hexafluoro-3,5-xylyl)-4-isothiazolecarboxylic acid and 20 ml (32.8 g, 0.276 mol) of thionyl chloride was held at reflux on a steam bath for 0.5 hours and was concentrated under vacuum to 7.6 g of acid chloride, an oil.

A solution of 2.50 g of acid chloride and 10 ml of methanol was held at reflux for 0.5 hours, filtered, and concentrated to 90° (0.4 torr) to 2.23 g (90% yield) of oil, $n_D^{23}=1.4966$, that slowly crystallized, m.p. 45°–46.5°.

Anal. Calc'd. for $C_{13}H_7F_6NO_2S$: C, 43.95; H, 1.99. Found: C, 44.12; H, 2.14.

EXAMPLE 27

Preparation of Ethyl 3-($\alpha,\alpha,\alpha,\alpha',\alpha',\alpha'$-Hexafluoro-3,5-Xylyl)-4-Isothiazolecarboxylate. Use of a similar procedure to that above gave the product in 96% yield as an oil, $n_D^{23}=1.4901$, that slowly crystallized, m.p. 61.5°–63°.

Anal. Calc'd. for $C_{14}H_9F_6NO_2S$: C, 45.53; H, 2.46. Found: C, 45.31; H, 2.51.

EXAMPLE 28

Preparation of Propyl 3-($\alpha,\alpha,\alpha,\alpha',\alpha',\alpha'$-Hexafluoro-3,5-Xylyl)-4-Isothiazolecarboxylate. A solution of 2.50 g of acid chloride and 10 ml of 1-propanol was heated on a steam bath for 2 hours, filtered, and concentrated under vacuum to 90° (0.4 torr) to give 2.52 g (94% yield) of oil, $n_D^{23}=1.4875$.

Anal. Calc'd. for $C_{15}H_{11}F_6NO_2S$: C, 47.00; H, 2.89. Found: C, 47.01; H, 2.86.

EXAMPLE 29

Preparation of Ethyl 3-(3,4-Dimethoxyphenyl)-4-Isothiazolecarboxylate. A solution of 29.7 g (0.112 mol) of acid and 70.3 g (5 equivalents) of thionyl chloride was heated on a steam bath for 0.75 hours, concentrated under vacuum, heated in 50 ml of ethanol at reflux for 45 minutes, concentrated under vacuum, and the residue was crystallized from ethanol-hexane to give 32.05 g (98%) of solid, m.p. 74°–75.5°.

Anal. Calc'd. for $C_{14}H_{15}NO_4S$: C, 57.32; H, 5.15. Found: C, 57.36; H, 5.14.

EXAMPLE 30

Preparation of Methyl 3-($\alpha,\alpha,\alpha$-Trifluoro-m-Tolyl)-4-Isothiazolecarboxylate. A solution of 2.92 g (0.010 mol) of 3-($\alpha,\alpha,\alpha$-trifluoro-m-tolyl)-4-isothiazolecarbonyl chloride prepared as in Example 29 and 10 ml of methanol was held at reflux for 0.5 hours and was concentrated under vacuum to 80° (0.3 torr) to 2.72 g of oil, $n_D^{23.4°}=1.5404$.

Anal. Calc'd. for $C_{12}H_8F_3NO_2S$: C, 50.17; H, 2.81. Found: C, 50.26; H, 2.88.

EXAMPLE 31

Preparation of 3-($\alpha,\alpha,\alpha$-Trifluoro-m-Tolyl)-4-Isothiazolecarboxylic Acid, Isopropyl Ester. A solution of 2.92 g (0.010 mol) of acid chloride prepared as in Example 29 and 10 ml of isopropyl alcohol was heated on a steam bath for 1.5 hours, filtered, and concentrated under vacuum to 90° (0.2 torr) to give 2.95 g of colorless oil, $n_D^{24}=1.5225$.

Anal. Calc'd. for $C_{14}H_{12}F_3NO_2S$: C, 53.33; H, 3.84. Found: C, 53.16; H, 3.77.

EXAMPLE 32

Preparation of 3-($\alpha,\alpha,\alpha$-Trifluoro-m-Tolyl)-4-Isothiazolecarboxylic Acid, 2,2,2-Trifluoroethyl Ester. A solution of 2.50 g (0.00856 mol) of 3-($\alpha,\alpha,\alpha$-trifluoro-m-tolyl)-4-isothiazolecarbonyl chloride and 50 ml of 2,2,2,-trifluoroethanol was held at reflux for 40 minutes, was allowed to stand overnight, and was concentrated under vacuum (to 90° at 0.1 torr) to give 2.68 g (88%) of oil, $n_D^{24}=1.4976$.

Anal. Calc'd. for $C_{13}H_7F_6NO_2S$: C, 43.95; H, 1.99. Found: C, 43.73; H, 1.98.

EXAMPLE 33

Preparation of 3-($\alpha,\alpha,\alpha$-Trifluoro-m-Tolyl)-4-Isothiazolecarboxylic Acid, 2,2,2-Trichloroethyl Ester. A solution of 2.0 g (0.0069 mol) of 3-($\alpha,\alpha,\alpha$-trifluoro-m-tolyl-4-isothiazolecarbonyl chloride and 1.22 g (1.18 equivalents) of 2,2,2-trichloroethanol was heated at 70°–140° in an oil bath for 6.5 hours. The reaction mixture was concentrated under vacuum to give 1.78 g of oil, $n_D^{23}=1.5499$ (yield 63.8%).

Anal. Calc'd. for $C_{13}H_7Cl_3F_3NO_2S$: C, 38.59; H, 1.74; N, 3.46. Found: C, 38.28; H, 1.69; N, 3.19.

EXAMPLE 34

Preparation of 3-($\alpha,\alpha,\alpha$-Trifluoro-m-Tolyl)-4-Isothiazolecarboxylic Acid, 2-Chloroethyl Ester. By a procedure similar to that used for Example 33, there was obtained 1.65 g of oil, $n_D^{23} = 1.5452$ (yield 72%).

Anal. Calc'd. for $C_{13}H_9ClF_3NO_2S$: C, 46.51; H, 2.70; N, 4.17. Found: C, 46.54; H, 2.55; N, 4.10.

EXAMPLE 35

Preparation of 3-($\alpha,\alpha,\alpha$-Trifluoro-m-Tolyl)-4-Isothiazolecarboxylic Acid, n-Octyl Ester. A solution of 1.0 g (0.0034 mol) of 3-($\alpha,\alpha,\alpha$-trifluoro-m-tolyl)-4-isothiazolecarbonyl chloride and 0.45 g (1 equivalent) of 1-octanol was heated on a steam bath for 2.0 hours. The reaction mixture was dissolved in ether, dried, filtered, and concentrated under vacuum to give 1.04 g of oil, $n_D^{23.2} = 1.5107$ (yield 78.7%).

Anal. Calc'd. for $C_{19}H_{22}F_3NO_2S$: C, 59.21; H, 5.75; N, 3.63. Found: C, 59.06; H, 5.60; N, 3.63.

EXAMPLE 36

Preparation of 3-($\alpha,\alpha,\alpha$-Trifluoro-m-Tolyl)-4-Isothiazolecarboxylic Acid, n-Hexyl Ester. By a procedure similar to that used for Example 35, using excess n-hexanol, there was obtained 0.91 g of oil, $n_D^{23} = 1.5094$ (yield 74.9%).

Anal. Calc'd. for $C_{17}H_{18}F_3NO_2S$: C, 57.13; H, 5.08; N, 3.92. Found: C, 57.67; H, 5.15; N, 3.68.

EXAMPLE 37

Preparation of 3-($\alpha,\alpha,\alpha$-Trifluoro-m-Tolyl-4-Isothiazolecarboxylic Acid, Allyl Ester. By a procedure similar to that used for Example 35, using excess alcohol, there was obtained 0.55 g of oil, $n_D^{23} = 1.5360$ (yield 51.6%).

Anal. Calc'd. for $C_{14}H_{10}F_3NO_2S$: C, 53.67; H, 3.22; N, 4.47. Found: C, 54.00; H, 3.56; N, 4.70.

EXAMPLE 38

Preparation of 3-($\alpha,\alpha,\alpha$-Trifluoro-m-Tolyl)-4-Isothiazolecarboxylic Acid, 2-Chloroallyl Ester. By a procedure similar to that used for Example 33, there was obtained 0.65 g of an oil, $n_D^{23.2} = 1.5468$ (yield 55%).

Anal. Calc'd. for $C_{14}H_9ClF_3NO_2S$: C, 48.36; H, 2.61; N, 4.03. Found: C, 48.26; H, 2.69; N, 4.06.

EXAMPLE 39

Preparation of 3-(m-Nitrophenyl)-4-Isothiazolecarboxylic Acid, Ethyl Ester. A solution of 1.5 (0.006 mol) of the free acid prepared in accordance with Scheme A and excess thionyl chloride was heated on a steam bath for 0.75 hours. The reaction mixture was concentrated under vacuum. A solution of the residue and 15 cc of ethanol was heated on a steam bath for 0.75 hours and cooled to give a solid. The solid was recrystallized twice from ethanol to give 1.0 g solid, m.p. 136.5°–138°. The first filtrate residue was crystallized from ethanol to give 0.2 g solid, m.p. 132°–136°. (Total yield 71.9%.)

Anal. Calc'd. for $C_{12}H_{10}N_2O_4S$: C, 51.79; H, 3.62; N, 10.07. Found: C, 51.85; H, 3.38; N, 10.07.

EXAMPLE 40

Preparation of 3-($\alpha,\alpha,\alpha$-Trifluoro-m-Tolyl)-4-Isothiazolecarboxylic Acid, Propyl Ester. A solution of 2.92 g (0.010 mol) of 3-($\alpha,\alpha,\alpha$-trifluoro-m-tolyl)-4-isothiazolecarbonyl chloride and 4 g (0.0667 mol) of 1-propanol was heated on a steam bath for 1 hour and was concentrated under vacuum to 70° (0.5 torr) to give 3.17 g of clear oil, $n_D^{20.8} = 1.5261$, infrared (film) 5.80$\mu$.

Anal. Calc'd. for $C_{14}H_{12}F_3NO_2S$: C, 53.33; H, 3.84. Found: C, 53.67; H, 4.01.

EXAMPLE 41

Preparation of 3-($\alpha,\alpha,\alpha$-Trifluoro-m-Tolyl)-4-Isothiazolecarboxylic Acid, Butyl Ester. A solution of 2.92 g (0.010 mol) of acid chloride and 0.80 g (0.0108 mol) of 1-butanol was heated in an oil bath at 110° for 2 hours and was concentrated under vacuum to 90° (0.4 torr) to give 3.01 g (91%) of oil, $n_D^{20.5} = 1.5221$, infrared (film) 5.80$\mu$.

Anal. Calc'd. for $C_{15}H_{14}F_3NO_2S$: C, 54.70; H, 4.28. Found: C, 54.46; H, 4.09.

EXAMPLE 42

Preparation of 3-($\alpha,\alpha,\alpha$-Trifluoromethyl-m-Tolyl)-4-Isothiazolecarboxylic Acid, 2-Butoxyethyl Ester. A solution of 2.92 g (0.010 mol) of acid chloride and 1.22 g (0.0103 mol) of 2-butoxyethanol was heated in an oil bath at 110°–115° for 3 hours and was concentrated under vacuum to 90° (0.04 torr) to 3.66 g of oil, $n_D^{22.4} = 1.5152$, infrared (film) 5.80$\mu$.

Anal. Calc'd. for $C_{17}H_{18}F_3NO_3S$: C, 54.68; H, 4.86. Found: C, 54.67; H, 4.80.

EXAMPLE 43

Preparation of 3-($\alpha,\alpha,\alpha$-Trifluoro-m-Tolyl)-4-Isothiazolecarboxylic Acid, m-Cumenyl Ester. A solution of 2.92 g (0.010 mol) of acid chloride and 1.36 g (0.010 mol) of pure m-isopropylphenol was heated in an oil bath at 115°–120° for 2 hours and was concentrated under vacuum at 90° (0.6 torr) to 3.90 g (100%) of oil, $n_D^{21} = 1.5611$, infrared (film) 5.74$\mu$.

Anal. Calc'd. for $C_{20}H_{16}F_3NO_2S$: C, 61.37; H, 4.12. Found: C, 61.22; H, 3.97.

EXAMPLE 44

Preparation of 3-(m-Chlorophenyl)-4-Isothiazolecarboxylic Acid, Ethyl Ester. Utilizing a procedure similar to Example 39, there was obtained a solid, m.p. 66.5°–68°.

Anal. Calc'd. for $C_{12}H_{10}ClNO_2S$: C, 53.83; H, 3.76. Found: C, 53.86; H, 3.73.

EXAMPLE 45

Preparation of 3-(3',4'-Dichlorophenyl)-4-Isothiazolecarboxylic Acid, Ethyl Ester. Utilizing the procedure of Example 39, there was obtained a solid, m.p. 111.5°–112°.

Anal. Calc'd. for $C_{12}H_9Cl_2NO_2S$: C, 47.70; H, 3.00. Found: C, 47.61; H, 3.02.

The 3-aryl-4-isothiazolecarboxylates of the invention may also be prepared by adding aryl Grignard reagents to alkyl cyanoacetate. The resultant $\beta$-aminocinnamates are converted to the carboxylate via a Vilsmeier-Haack reaction, thiation and oxidation. For purposes of clarity, Scheme B is provided below.

Scheme B

NCCH$_2$CO$_2$ alkyl ⟶

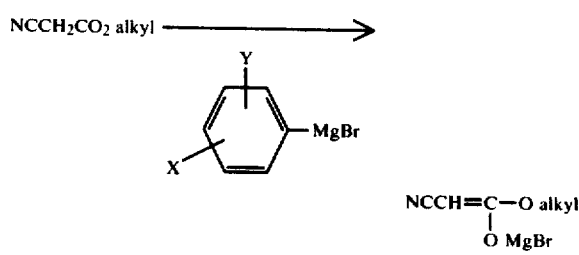

NCCH=C—O alkyl
|
O MgBr

-continued
Scheme B

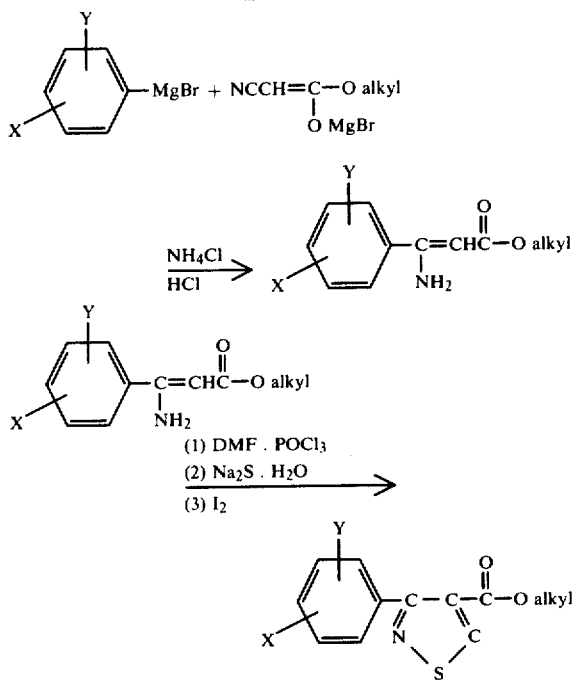

In accordance with Scheme B, 1.0 mole of alkyl cyanoacetate is treated with two moles of aryl magnesium bromide in ether while stirring at temperatures from −75° to room temperature. The mixture is then heated at reflux until gas chromatographic analysis of hydrolyzed aliquots of the reaction mixture revealed the reaction to be complete. Then, the reaction mixture is cooled to about 10° or below and poured slowly into a 1.7 liter mixture of ice-water containing 2.0 moles of $NH_4Cl$. This mixture is shaken with an ice-cold solution of 2.0 moles of HCl in 500 ml of water. The layers are separated and the aqueous layer is then extracted with ether. The ether layers are combined, dried ($CaSO_4$), and concentrated under vacuum to give crude alkyl β-aminocinnamate.

To a solution of 0.10 moles of the appropriate alkyl β-aminocinnamate in 90 ml of dimethylformamide is added 0.10 moles of phosphorous oxychloride while stirring at −60° under dry $N_2$. After warming to about 15°-25°, the mixture is stirred at about 25° for about ten minutes. The solution is then poured into an ice-cold solution of 0.11 moles of $Na_2S.9H_2O$ in 110 ml of water. The resultant mixture is stirred for about five minutes and extracted with benzene. The benzene layers are dried ($CaSO_4$) and then 0.1 moles of $I_2$ in 200 ml of benzene is then added at 20°-30°. The dark benzene solution is then washed with an aqueous $K_2CO_3$ solution and an aqueous solution of $Na_2S_2O_3$. A third washing with an aqueous $K_2CO_3$ solution, drying ($CaSO_4$) and concentration under vacuum gives the crude isothiazolecarboxylate.

In order to illustrate the preparation of the 3-aryl-4-isothiazolecarboxylates by the methods of Scheme B, the following examples are presented.

The preparation of β-aminocinnamates is illustrated by Examples 46-50.

EXAMPLE 46

Preparation of Ethyl β-Aminocinnamate. Bromobenzene (235 g, 1.5 mol) in 200 ml of anhydrous ether was added dropwise, with stirring, to 36.5 g of magnesium turnings (1.5 mol) in about 400 ml of ether according to literature methods. When addition was complete, the mixture was heated at reflux for one hour and then cooled to <20°. To the cooled Grignard reagent was added dropwise, with stirring, 0.5 equivalents of ethyl cyanoacetate (84.9 g, 0.75 mol). The temperature was kept below 20° by cooling in ice. During the addition, the formation of a gelatinous solid was noted. On completion of addition of the ester, a 2-ml aliquot of the reaction mixture was hydrolyzed with saturated $NH_4Cl$; gas chromatography of the ether layer showed that some product was already present. The reaction mixture was heated to reflux for 19 hours. Hydrolysis of the mixture with 1500 ml of ice-cold saturated $NH_4Cl$ was exothermic. Extraction of this mixture with ether proved very difficult due to the presence of a persistent gummy emulsion, until it was determined that addition of 2 N HCl to just the emulsion in the separatory funnel, only to the point of separation into 2 neat layers, would result in a pH decrease to about 7-7.5 without destroying the desired product. The ether extracts were dried ($CaSO_4$) and concentrated under reduced pressure to yield 127.7 g of gold-yellow residue, which was vacuum distilled twice to give 86.01 g (60% yield by weight) of pure material, boiling point 110°-112° (0.2 mm).

EXAMPLE 47

Preparation of Ethyl β-Amino-m-Trifluoromethylcinnamate. Phenylmagnesium bromide was prepared from 70 g (0.445 mol) of bromobenzene and 11.1 g (0.458 mol) of magnesium in 300 ml of ether. Then, 50.3 g (0.445 mol) of ethyl cyanoacetate was added dropwise with stirring at −55° to −35° (vigorous exothermic reaction after about 20-30% of the ethyl cyanoacetate added, even with Dry ice-acetone bath cooling). A very heavy precipitate formed that prevented stirring. The mixture was allowed to warm to 15°.

A solution of m-(trifluoromethyl)phenylmagnesium bromide, prepared from 100 g (0.445 mol) of m-bromobenzotrifluoride and 11.1 g (0.458 mol) of magnesium, in 300 ml of ether was added to the above mixture. The resultant mixture was stirred at reflux for 44 hours and then was cooled. A solution of 53 g (1.0 mol) of $NH_4Cl$ in 300 ml of water was added slowly with stirring at 10°-20°, and then 0.90 mol of 2 N HCl was slowly added. The layers were shaken together in a separatory funnel and were separated. The aqueous layer was extracted with two 250-ml portions of ether. The ether layers were combined, dried ($CaSO_4$), and concentrated under vacuum to 95.7 g of black oil. Gas chromatography assay of this oil on a 10 ft. 5% SE-30 column at 220° showed there was less than 1% (none detected) of ethyl β-aminocinnamate in the ethyl β-amino-m-trifluoromethylcinnamate, which elutes first. Gas chromatography assay of a weighed aliquot of the oil with a weighed quantity of o-dichlorobenzene and use of a calibration mixture revealed that the 95.7 g of oil contained 74.8% product (62% yield). Distillation of the oil gave 72.9 g of 94% pure product (60% yield), boiling point 110°-115° (0.05 torr). Redistillation of a small amount of this material gave a 99-100% pure sample, boiling point 106°-107° (0.06 torr).

Anal. Calc'd. for $C_{12}H_{12}F_3NO_2$: C, 55.60; H, 4.67. Found: C, 55.42; H, 4.36.

EXAMPLE 48

Preparation of Ethyl β-Amino-p-Trifluoromethylcinnamate. To the Grignard reagent prepared from 98 g (0.436 mol) of p-bromobenzotrifluoride and 10.59 g (0.436 mol) of magnesium in ether was added 24.65 g (0.218 mol) of ethyl cyanoacetate dropwise with stirring and cooling in an ice bath. The resultant mixture was stirred at reflux for 24 hours. The usual workup gave 49.4 g of dark red-brown residue; distillation of this material gave 16.73 g (30%) of product, boiling point 120°–123° (0.15 torr).

Anal. Calc'd. for $C_{12}H_{12}F_3NO_2$: C, 55.60; H, 4.67. Found: C, 56.67; H, 4.63.

EXAMPLE 49

Preparation of Ethyl β-Amino-m-Methylcinnamate. To 202 ml of 2.9 M phenylmagnesium bromide in ether (0.585 mol) was added 100 ml of ether. Then, 66.1 g (0.585 mol) of ethyl cyanoacetate was added over a few minutes with stirring at −40° to −15°. A heavy, thick precipitate formed that made stirring difficult. The mixture was allowed to warm slowly to 20°. Then, the Grignard reagent prepared from 100 g (0.585 mol) of 3-bromotoluene and 14.4 g (0.593 mol) of magnesium turnings in 300 ml of ether was added. The mixture was stirred at reflux for 4 hours, cooled, and poured slowly with stirring into 1 l. of ice-water mixture in which 62.6 g (1.17 mol) of $NH_4Cl$ was dissolved. Then, an ice-cold solution of 1.17 mol of HCl in 300 ml of water was added with stirring. The two layers were shaken together and separated. The aqueous layer was extracted with two 200-ml portions of ether. The ether layers were combined, dried ($CaSO_4$), and concentrated under aspirator vacuum to 112.0 g of oil that contained 78.4 g (65% yield) of product (gas chromatography assay with internal standard). The oil was distilled to give 83.2 g of 89% pure product (62% yield of ester), boiling point 120°–130° (0.08 torr). Redistillation of the product through a fractionating column gave 57.2 g (48%) of 97% pure product, boiling point 118° (0.05 torr). A small sample was redistilled to give 100% pure material, boiling point 118° (0.1 torr).

Anal. Calc'd. for $C_{12}H_{15}NO_2$: C, 70.22; H, 7.37. Found: C, 70.31; H, 7.44.

EXAMPLE 50

Preparation of Ethyl β-Amino-m-Isopropylcinnamate. To the Grignard reagent prepared from 39.5 g (0.198 mol) of m-bromocumene and 4.9 g (0.20 mol) of magnesium in 150 ml of ether was added 11.2 g (0.099 mol) of ethyl cyanoacetate dropwise with stirring at 10°. The mixture was stirred at reflux for 22 hours and was allowed to stand at 23° for four days. Then, 10.6 g (0.20 mol) of $NH_4Cl$ in 60 ml of water was added with stirring at 10°–15°, followed by 0.20 mol of 2 N, HCl at 0°. The layers were separated, and the water layer was extracted with 100 ml of ether. The ether layers were combined, extracted with dilute $NaHCO_3$ solution, dried ($CaSO_4$), and distilled to give 4.95 g of 80% pure product, boiling point 139°–142° (0.15 torr) and 0.87 g of about 97% pure product, boiling point 142°–143° (0.15 torr). [Infrared analysis of the lower-boiling impurity indicated it to be bi(m-cumenyl)].

Anal. Calc'd. for 97% $C_{14}H_{19}NO_2$-3% $C_{18}H_{22}$: C, 72.60; H, 8.24; N, 5.82. Found: C, 72.60; H, 8.46; N, 5.84.

Preparation of 3-aryl-4-isothiazolecarboxylates from the β-aminocinnamates is illustrated by Examples 51–55.

EXAMPLE 51

Preparation of Ethyl 3-Phenyl-4-Isothiazolecarboxylate. 1.91 g of ethyl β-aminocinnamate (0.01 mol) and 6 ml of dimethyl formamide (5.68 g, 0.073 mol) were cooled to −60°, with stirring. Then 1.533 g (0.917 ml, 0.01 mol) of $POCl_3$ was added and the mixture allowed to warm up exothermically to about 25°. It was then poured into an ice-cold solution of 2.40 g $Na_2S$ nonahydrate (0.01 mol) in 10 ml of $H_2O$. This mixture was extracted three times with benzene. The benzene solution was dried ($CaSO_4$). A mixture of 3.03 g of $I_2$ in 50 ml of benzene was added to this material, dropwise with stirring; stirring was continued for 10 minutes more. It was extracted twice with 10% $Na_2CO_3$ and then twice with 5% $Na_2S_2O_3$. The benzene was dried ($CaSO_4$), concentrated, and the residue redissolved in about 30 ml benzene plus 6.00 g of o-dichlorobenzene (internal gas chromatography standard) and assayed (gas chromatography) for percent product (best yield, 72.0%).

EXAMPLE 52

Preparation of 3-(m-Cumenyl)-4-Isothiazolecarboxylic Acid. To 5.8 g of about 80% pure ethyl β-amino-m-isopropylcinnamate (about 0.02 mol) in 18 ml of DMF was added slowly 2.28 ml (3.82 g, 0.025 mol) of $POCl_3$ with stirring at −60°. The mixture was allowed to warm; an exothermic reaction carried the temperature to 0°. The mixture was stirred for 10 minutes at 20° and was poured into a cold solution of 7.20 g (0.030 mol) of $Na_2S.9H_2O$ in 30 ml of water. This mixture was stirred for 5 minutes and was extracted with three 40-ml portions of benzene. The benzene layers were combined, dried ($CaSO_4$), treated with 6.35 g (0.025 mol) of $I_2$ in 120 ml of benzene, stirred for 5 minutes, extracted three times with aqueous $NaHCO_3$ solution and twice with aqueous sodium thiosulfate solution, and concentrated under vacuum to 6.1 g of an oil that was a 16:84 mixture (gas chromatography assay). The oil was heated with 4.0 g (0.10 mol) of NaOH in 80 ml of 50% aqueous ethanol at reflux for 1 hour. The solution was concentrated under vacuum, diluted with 200 ml of water, extracted three times with ether, and acidified with 17 ml of concentrated HCl (0.20 mol). The resultant mixture was extracted three times with ether. These three ether extracts were combined and concentrated under vacuum. The residue was crystallized from aqueous ethanol to give 2.96 g (60%) of solid, m.p. 143°–157°. The solid was recrystallized from 1,2-dichloroethane to give 2.04 g of solid, m.p. 157°–159°. Recrystallization of this material from 1,2-dichloroethaneheptane (charcoal) gave a white solid, m.p. 158°–160°.

Example 52 illustrates the preparation of the free acid from which the ester may be prepared as illustrated in Example 53. The acid is prepared as an acid to purification.

EXAPLE 53

Preparation of Ethyl 3-(m-Cumenyl)-4-Isothiazolecarboxylate. A mixture of 1.50 g (0.00608 mol) of 3-(m-cumenyl)-4-isothiazolecarboxylic acid and 5 ml (8.2 g, 0.069 mol) of thionyl chloride was heated at reflux on a steam bath for 30 minutes and was concentrated under vacuum. The residue was heated in 15 ml of ethanol at reflux for 15 minutes; the solution was filtered and concentrated under vacuum to 90° (0.3 torr) to give 1.53 g (92%) of oil, $n_D^{23°} = 1.5693$.

Anal. Calc'd. for $C_{15}H_{17}NO_2S$: C, 65.43; H, 6.22. Found: C, 65.46; H, 6.30.

EXAMPLE 54

Preparation of 3-($\alpha,\alpha,\alpha$-Trifluoro-p-Tolyl)-4-Isothiazolecarboxylic Acid. Using the same procedure of Example 51 but starting with 16.2 g of ethyl β-amino-p-trifluoromethylcinnamate gave 17.09 g of crude ethyl 3-($\alpha,\alpha,\alpha$-trifluoro-p-tolyl)-4-isothiazolecarboxylate. This material was heated with five equivalents of NaOH in 50 ml of water at reflux for 5 hours. The solution was cooled, extracted with ether, acidified with HCl, and extracted with ether. The latter ether extract was dried ($CaSO_4$) and concentrated under vacuum. The residue was crystallized three times from 1,2-dichloroethane to give 4.0 g (23%) of solid, m.p. 195°–196°.

Anal. Calc'd. for $C_{11}H_6F_3NO_2S$: C, 48.35; H, 2.21. Found: C, 48.39; H, 2.24.

EXAMPLE 55

Preparation of Ethyl 3-($\alpha,\alpha,\alpha$-Trifluoro-p-Tolyl)-4-Isothiazolecarboxylate. A solution of 2.5 g (0.0091 mol) of acid and 5.36 g (five equivalents) of thionyl chloride was heated for 0.5 hours on a steam bath and concentrated under vacuum. The residue was heated in 50 ml of ethanol at reflux for 1 hour. Concentration of the solution and crystallization of the residue from ethanol gave 1.41 g (51%) of solid, m.p. 63°–64°.

Anal. Calc'd. for $C_{13}H_{10}F_3NO_2S$: C, 51.82; H, 3.35. Found: C, 51.77; H, 3.35.

A third route for the preparation involves the thermolysis of the oxathiazol-2-ones prepared in accordance with Examples 1-5 with alkyl propiolate. Scheme C illustrates this method of preparation.

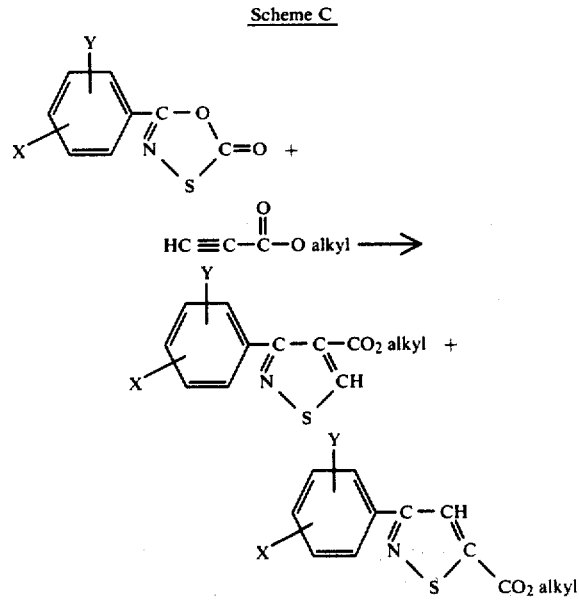

Scheme C

Scheme C is exemplified below in Examples 56–59.

EXAMPLE 56

Preparation of Ethyl 3-($\alpha,\alpha,\alpha$-Trifluoro-m-Tolyl)-4-Isothiazolecarboxylate. A solution of 12.36 g (0.050 mol) of 5-($\alpha,\alpha,\alpha$-trifluoro-m-tolyl)-1,3,4-oxathiazol-2-one and 19.62 g (0.20 mol) of ethyl propiolate in 75.0 g of o-dichlorobenzene was held at reflux under $N_2$ for 20 hours, at which time analysis by gas chromatography revealed that the reaction was complete and that the 4-carboxylate and the 5-carboxylate had formed in 46% and 39% yields, respectively. Concentration of the solution under vacuum gave 16.4 g of dark oil. Crystallization of the oil from 35 ml of ethanol at −20° gave 5.05 g (34%) of tan solid, m.p. 77°–79°, that was about 98% pure 5-carboxylate (gas chromatography assay). Concentration of the filtrate gave 10.8 g of oil. Chromatography of the oil on 550 g of silicic acid with benzene gave 5.2 g of 4-carboxylate that was 97% pure (3% low boilers, no 5-carboxylate present; gas chromatography analysis); infrared ($CHCl_3$), 5.83μ; nmr ($CDCl_3$) δ 9.43 (s, 1, 5-$\underline{H}$), 8.03-7.43 (m, 4, Ar$\underline{H}$), 4.30 (q, 2, J=7 Hz, OC$\underline{H}_2$CH$_3$), 1.23 (t, 3, J=7 Hz, OCH$_2$C$\underline{H}_3$).

Anal. Calc'd. for $C_{13}H_{10}F_3NO_2S$: C, 51.82; H, 3.35. Found: C, 52.09; H, 3.50.

The chromatography also gave 0.31 g (2%) of pure 5-carboxylate, m.p. 80°–81.5°. Recrystallization of the 5.05 g of 5-carboxylate from ethanol gave 4.05 g (27%) of colorless crystals, m.p. 80°–81.5°; infrared ($CHCl_3$) 5.81μ; nmr δ 8.20 (s, 1, 4-$\underline{H}$), 8.30-7.47 (m, 4, Ar$\underline{H}$), 4.47 (q, 2, J=7 Hz, OC$\underline{H}_2$CH$_3$), 1.43 (t, 3, J=7, Hz, OCH$_2$C$\underline{H}_3$).

Anal. Calc'd. for $C_{13}H_{10}F_3NO_2S$: C, 51.82; H, 3.35. Found: C, 51.98; H, 3.39.

EXAMPLE 57

Preparation of Ethyl 3-(p-Cyanophenyl)-4-Isothiazolecarboxylate. A solution of 10.2 g (0.050 mol) of 5-(p-cyanophenyl)-1,3,4-oxathiazol-2-one and 19.62 g (0.20 mol) of ethyl propiolate in 75.0 g of o-dichlorobenzene was held at reflux under $N_2$ for 20 hours, at which time gas chromatography analysis indicated that the 4-carboxylate and the 5-carboxylate had formed in 44% and 46% yields, respectively. Concentration of the reaction mixture under vacuum gave 20.3 g of brown solid. Crystallization of this material from ethanol gave 5.54 g (43%) of 5-carboxylate as a beige solid, m.p. 175°–179°. Crystallization of the solid from ethanol gave 0.1 g of unidentified, fairly insoluble white solid, m.p. 236°–237°, infrared ($CHCl_3$) 4.50, 5.81μ. The residue from the filtrate was chromatographed on silica gel with benzene, and the purest fractions were crystallized from ethanol to give 1.27 g (10%) of 5-carboxylate as a white solid, m.p. 183°–184.5°; infrared ($CHCl_3$) 4.50, 5.81μ; nmr ($CDCl_3$) δ 8.17 (s, 1, 4-$\underline{H}$), 7.93 (AA'BB' m, 4, Ar$\underline{H}$), 4.43 (q, 2, J=7 Hz, OC$\underline{H}_2$CH$_3$), 1.40 (t, 3, J=7 Hz, OCH$_2$C$\underline{H}_3$).

Anal. Calc'd. for $C_{13}H_{10}N_2O_2S$: C, 60.45; H, 3.90. Found: C, 60.49; H, 3.98.

The filtrate from the crystallization of the 20.3 g of brown solid was concentrated under vacuum, and the residue was chromatographed on silica gel with benzene. The 4-carboxylate thus obtained was crystallized from heptane to give 4.06 g (32%) of white solid, m.p. 109°–110°; infrared ($CHCl_3$) 4.50, 5.81μ; nmr ($CDCl_3$) δ 9.40 (s, 1, 5-$\underline{H}$), 7.73 (s, 4, Ar$\underline{H}$), 4.30 (q, 2, J=7 Hz, OC$\underline{H}_2$CH$_3$), 1.27 (t, 3, J=7 Hz, OCH$_2$C$\underline{H}_3$).

Anal. Calc'd. for $C_{13}H_{10}N_2O_2S$: C, 60.45; H, 3.90. Found: C, 60.48; H, 3.96.

EXAMPLE 58

Preparation of Ethyl 3-(p-Chlorophenyl)-4-Isothiazolecarboxylate. A solution of 10.68 g (0.050 mol) of 5-(p-chlorophenyl)-1,3,4-oxathiazol-2-one and 19.62 g (0.20 mol) of ethyl propiolate in 75 g of o-dichlorobenzene was held at reflux (150°) under $N_2$ for 10 hours and was concentrated under vacuum to 90° at 0.2 mm to give 16.0 g of black oil. Dry column chromatography of the oil on silica gel with benzene and crystallizations of the fractions rich in 5-carboxylate gave 3.50 g (26% yield) of pure ethyl 3-(p-chlorophenyl)-5-isothiazolecarboxylate, m.p. 87.5°–89° (from ethanol); nmr (CDCl$_3$) δ 8.13 (s, 1, 4-H), 7.7 (m, 4, ClC$_6$H$_4$), 4.47 (q, 2, J=7 Hz, OCH$_2$CH$_3$), 1.43 (t, 3, J=7 Hz, OCH$_2$CH$_3$).

Anal. Calc'd. for $C_{12}H_{10}ClNO_2S$: C, 53.83; H, 3.76. Found: C, 53.84; H, 3.64.

Crystallization of the fractions rich in 4-carboxylate from aqueous ethanol gave 2.45 g (18% yield) of pure ethyl 3-(p-chlorophenyl)-4-isothiazolecarboxylate, m.p. 70.5°–71.5°.

EXAMPLE 59

Preparation of Ethyl 3-(3,5-Dimethoxyphenyl)-4-Isothiazolecarboxylate. By a procedure similar to that employed above, ethyl 3-(3,5-dimethoxyphenyl)-4-isothiazolecarboxylate was obtained in 25% yield as a white solid, m.p. 71.5°–73° (from ethanol); nmr (CDCl$_3$) δ 9.23 (s, 1, 5-H), 6.72 (d, 2, J=2 Hz, ArH), 6.48 (t, 1, J=2 Hz, ArH), 4.23 (q, 2, J=7 Hz, OCH$_2$CH$_3$), 3.78 (s, 6, OCH$_3$), 1.23 (t, 3, J=7 Hz, OCH$_2$CH$_3$).

Anal. Calc'd. for $C_{14}H_{15}NO_4S$: C, 57.32; H, 5.15. Found: C, 57.40; H, 5.21.

Ethyl 3-(3,5-dimethoxyphenyl)-5-isothiazolecarboxylate was obtained in 32% yield as a white solid, m.p. 101°–103° (from ethanol), nmr (CDCl$_3$) 7.98 (s, 1, 4-H), 7.03 (d, 2, J=2 Hz, ArH), 6.47 (t, 1, J=2 Hz, ArH), 4.37 (q, 2, J=7 Hz, OCH$_2$CH$_3$), 3.82 (s, 6, OCH$_3$), 1.40 (t, 3, J=7 Hz, OCH$_2$CH$_3$).

Anal. Calc'd. for $C_{14}H_{15}NO_4S$: C, 57.32; H, 5.15. Found: C, 57.50; H, 5.17.

Another preparation of 3-aryl-4-isothiazolecarboxylates involves the reaction of oxathiazol-2-ones with alkyl chloroacrylate as illustrated by Scheme D.

Scheme D

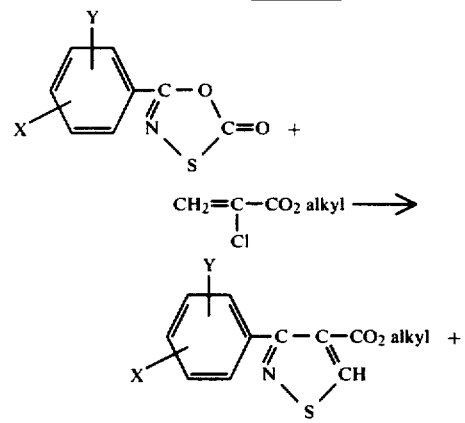

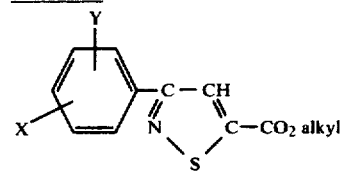

Example 60 is illustrative of the preparation of 3-aryl-4-isothiazolecarboxylates using the method of Scheme D.

EXAMPLE 60

Preparation of 3-(p-Chlorophenyl)-4-Isothiazolecarboxylates. A solution of 40.4 g (0.30 mol) of ethyl 2-chloroacrylate and 2.14 g (0.010 mol) of 5-(p-chlorophenyl)-1,3,4-oxathiazole-2-one in 75 g of o-dichlorobenzene was held at reflux (165°–175°) for 55 minutes, at which time gas chromatography analysis indicated about 70% reaction. The reaction mixture was allowed to cool, and the supernatant was decanted from polymeric ester. Concentration of the supernatant under vacuum, chromatography of the residue on silicic acid, and crystallizations of the various materials thus obtained gave 0.30 g (16%) of ethyl 3-(p-chlorophenyl)-4-isothiazolecarboxylate, m.p. 69°–70°, and 0.31 g (17%) of ethyl 3-(p-chlorophenyl)-5-isothiazolecarboxylate, m.p. 87°–89°.

Salts of the isoxazole-4-carboxylic acid may be prepared by neutralization of the appropriate acid with the appropriate base. The acid may be prepared in accordance with Scheme A or an ester prepared by any of the other methods may be hydrolyzed to the free acid.

EXAMPLE 61

Preparation of 3-(α,α,α-Trifluoro-m-Tolyl)-4-Isothiazolecarboxylic Acid, Potassium Salt. A solution of 1.91 g (0.0070 mol) carboxylic acid and 0.462 g of 85% KOH (0.0070 mol) in 12 ml of water was concentrated under vacuum to 1.9 g (87%) of white solid, m.p. 276°–277°; infrared (mineral oil mull) 6.30μ.

Anal. Calc'd. for $C_{11}H_5F_3KNO_2S$: C, 42.44; H, 1.62. Found: C, 42.51; H, 1.63.

EXAMPLE 62

Preparation of 3-(α,α,α-Trifluoro-m-Tolyl)-4-Isothiazolecarboxylic Acid, Isopropylamine Salt. To a solution of 2.73 g (0.010 mol) of carboxylic acid in 30 ml of ether was added 0.59 g (0.010 mol) of isopropylamine with swirling. After several seconds, copious precipitation of a white solid occurred. The solid was collected and washed with ether to give 2.7 g of white solid, m.p. 145°–147°.

Anal. Calc'd. for $C_{14}H_{15}F_3N_2O_2S$: C, 50.60; H, 4.55. Found: C, 50.57; H, 4.63.

EXAMPLE 63

Preparation of 3-(α,α,α-Trifluoro-m-Tolyl)-4-Isothiazolecarboxylic Acid, Dodecylamine Salt. A solution of 2.70 g (0.0099 mol) of carboxylic acid and 1.83 g (0.0099 mol) of dodecylamine in 30 ml of ether was filtered and concentrated under vacuum to 4.53 g of viscous oil that slowly crystallized, m.p. 43°–45°.

Anal. Calc'd. for $C_{23}H_{33}F_3N_2O_2S$: C, 60.24; H, 7.25. Found: C, 60.05; H, 7.12.

Additionally, esters have been prepared from the free acid prepared in accordance with Scheme A. These esters have been prepared by various procedures illustrated by Examples 64–67.

EXAMPLE 64

Preparation of Ethyl 3-(p-Tolyl)-4-Isothiazolecarboxylate. 3-(p-Tolyl)-4-isothiazolecarboxylic acid (1.5 g, 0.0068 mol), 20 ml of absolute ethanol, and boron trifluoride etherate (4.3 ml, 0.034 mol) were heated at reflux for 24 hours. Volatile materials were removed under reduced pressure. Water (25 ml) was added and the material extracted four times with ether. The ether was back-extracted with 5% NaHCO$_3$, dried (CaSO$_4$) and concentrated under reduced pressure to yield 1.51 g (0.0061 mol, 89.9%) of oil, n$_D^{25}$ = 1.5671.

Anal. Calc'd. for C$_{13}$H$_{13}$NO$_2$S: C, 63.13; H, 5.30. Found: C, 62.95; H, 5.52.

EXAMPLE 65

Preparation of Ethyl 3-(p-Nitrophenyl)-4-Isothiazolecarboxylate. 3-(p-Nitrophenyl)-4-isothiazolecarboxylic acid (1.5 g, 0.006 mol), plus one equivalent (2.51 g) of benzyl trimethylammonium hydroxide (40% in methanol) and excess ethyl iodide were heated just to reflux in hexamethylphoramide. The product was recrystalliced twice from ethanol to yield 0.24 g (.00086 mol, 14.3%) of ester, m.p. 150.5°–152.5°.

Anal. Calc'd. for C$_{12}$H$_{10}$N$_2$O$_4$S: C, 51.79; H, 3.62. Found: C, 52.35; H, 3.70.

EXAMPLE 66

Preparation of Glycolic Acid, Ethyl Ester, 3-(α,α,α-Trifluoro-m-Tolyl)-4-Isothiazolecarboxylate. To a mixture of 1.36 g (0.0050 mol) of 3-(α,α,α-trifluoro-m-tolyl)-4-isothiazolecarboxylic acid in 10 ml of hexamethylphosphoric triamide was added 0.80 g of 50% NaOH (0.010 mol), followed by 3.1 g (0.0254 mol) of ethyl chloroacetate. The mixture was stirred vigorously for 18 hours, diluted with water, and extracted twice with 40-ml portions of ether. The combined ether layers were washed twice with water, three times with aqueous K$_2$CO$_3$ solution, again with water, dried (CaSO$_4$), and concentrated under vacuum to 90° at 0.3 torr to give 1.5 g of 87% pure product as an oil. This oil was chromatographed on 130 g of Woelm silica gel (for dry column chromatography) in a 30 mm diameter column with 30% CHCl$_3$ in benzene. There was obtained 0.43 g of colorless liquid, n$_D^{22.8°}$ = 1.5241, that was 100% pure product.

Anal. Calc'd. for C$_{15}$H$_{12}$F$_3$NO$_4$S: C, 50.14; H, 3.37. Found: C, 50.06; H, 3.28.

EXAMPLE 67

Preparation of Lactic Acid, Ethyl Ester, 3-(α,α,α-Trifluoro-m-Tolyl)-4-Isothiazolecarboxylic. By a procedure similar to that used for Example 66, there was obtained 1.7 g of oil, n$_D^{23}$ = 1.5169 (yield 66.5%)

Anal. Calc'd. for C$_{16}$H$_{14}$F$_3$NO$_4$S: C, 51.47; H, 3.78; N, 3.75. Found: C, 51.20; H, 3.48; N, 3.73.

3-Phenyl-4-isothiazolecarbonyl chlorides may be prepared by reaction of the free acid with thionyl chloride as discussed in Scheme A.

EXAMPLE 68

Preparation of 3-(α,α,α-Trifluoro-m-tolyl)-4-Isothiazolecarbonyl Chloride. A mixture of 27.3 g (0.10 mol) of 3-(α,α,α-trifluoro-m-tolyl)-4-isothiazolecarboxylic acid and 20 ml (32.8 g, 0.276 mol) of thionyl chloride (purified by distillation from a little triphenyl phosphite) was heated on a steam bath for 40 minutes and then was concentrated under vacuum to remove excess SOCl$_2$. The resultant 27.3 g of product was crystallized from heptane to give 25.5 g (87%) of white solid, m.p. 76°–77.5°, infrared (CH$_2$Cl$_2$) 5.70μ.

Anal. Calc'd. for C$_{11}$H$_5$ClF$_3$NOS: C, 45.30; H, 1.73. Found: C, 45.41; H, 1.65.

3-Phenyl-4-isothiazolecarboxamides may be prepared by reaction of the acid chloride with ammonia or the appropriate amine.

EXAMPLE 69

Preparation of 3-(α,α,α-Trifluoro-m-Tolyl)-4-Isothiazolecarboxamide. A solution of 2.92 g (0.010 mol) of 3-(α,α,α-trifluoro-m-tolyl)-4-isothiazolecarbonyl chloride in 10 ml of THF was added to a solution of excess ammonia gas in THF stirred in a dry ice acetone bath. The mixture was slowly warmed to 23° with stirring. The solid NH$_4$Cl was removed by filtration, and the filtrate was concentrated to about 20 ml. Then 100 ml of ether was added, and the solution was extracted with two portions of 10% Na$_2$CO$_3$ solution and once with saturated NaCl solution. The ether layer was dried (CaSO$_4$) and concentrated to 2.25 g (83%) of white solid, m.p. 141°–141.5°; infrared (mineral oil mull) 2.92, 3.11, 6.09, 6.11μ.

Anal. Calc'd. for C$_{11}$H$_7$F$_3$N$_2$OS: C, 48.53; H, 2.59. Found: C, 48.73; H, 2.75.

EXAMPLE 70

Preparation of 3-(α,α,α-Trifluoro-m-Tolyl)-4-Isothiazolecarboxylic Acid, Isopropyl Amide. To a solution of 1.0 g (0.0034 mol) of 3-(α,α,α-trifluoro-m-tolyl)-4-isothiazolecarbonyl chloride and 20 cc of THF was added 0.45 g (2.1 equivalents) of isopropylamine. The reaction mixture was heated on a steam bath for 20 minutes. The isopropylamine hydrochloride was filtered off and the filtrate was concentrated to a solid. The solid was washed with H$_2$O, dissolved in THF, dried (CaSO$_4$), and concentrated under vacuum to give 0.94 g of solid. The solid was recrystallized from EtOAc/hexane to give 0.4 g white solid, m.p. 166°–167°. The filtrates gave another 0.3 g of white solid, m.p. 166.5°–168°. (Total yield = 88%).

Anal. Calc'd. for C$_{14}$H$_{13}$F$_3$N$_2$OS: C, 53.50; H, 4.17; N, 8.91. Found: C, 53.61; H, 4.10; N, 8.92.

EXAMPLE 71

Preparation of 3-(α,α,α-Trifluoro-m-Tolyl)-4-Isothiazolecarboxylic Acid, Diethylamide. By a procedure similar to that used for Example 70, there was obtained 0.97 g of a yellow oil, n$_D^{23}$ = 1.5383. (yield 86.9%).

Anal. Calc'd. for C$_{15}$H$_{15}$F$_3$N$_2$OS: C, 54.87; H, 4.60; N, 8.53. Found: C, 54.93; H, 4.96; N, 8.59.

The isoxazolecarboxylates of the foregoing formula can be prepared by 1,3-dipolar cycloaddition of nitrile oxides, formed in situ from hydroxamoyl chlorides, to alkyl β-pyrrolidinylacrylates. Scheme E illustrates the preparation of said isoxazolecarboxylates.

Scheme E

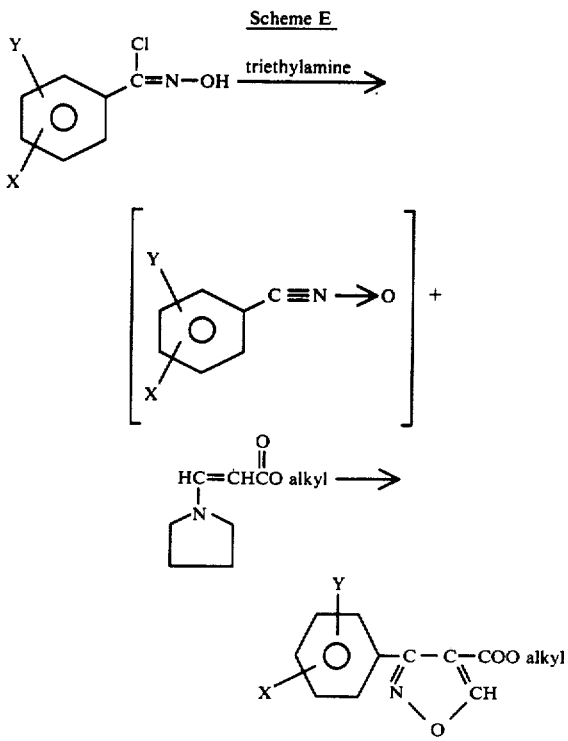

Alkyl β-pyrrolidinylacrylate may be prepared by the addition of pyrrolidine to alkyl propiolate. Hydroxamoyl chloride may be prepared by the addition of chlorine to the appropriate benzaldoxime.

Examples 72-79 are presented in order to illustrate the preparation of the isoxazolecarboxylates to the invention.

EXAMPLE 72

Preparation of Ethyl β-Pyrrolidinylacrylate. A solution of 29.43 g of ethyl propiolate (0.30 mol) in 200 ml of benzene was held at 25° in a water bath with magnetic stirring. A solution of 21.34 g of pyrrolidine in 50 ml of benzene was added dropwise over a period of 45 minutes, during which time the temperature rose to 35°. The clear brown solution was stirred overnight and the solvent removed under reduced pressure at 55°. The residue was distilled under reduced pressure to give 35.05 g of yellow oil, boiling point 110° (0.4 torr), which crystallized upon standing. The yellow solid was recrystallized from petroleum ether to give 31.36 (62%) of yellowish platelets, m.p. 37.5°-39.5°.

EXAMPLE 73

Preparation of m-Trifluoromethylbenzohydroxamoyl Chloride. A solution of 15.70 g of m-trifluoromethylbenzaldoxime (0.082 mol) in 40 ml of chloroform was cooled with magnetic stirring to −5° in ice-MeOH. A gentle stream of $Cl_2$ was passed into the solution, while the temperature was maintained below 0°, until addition of more $Cl_2$ did not produce a green color. The mixture was stirred for two hours and allowed to warm to room temperature. The solvent was removed by evaporation under reduced pressure at 50° and the oily product recrystallized twice from petroleum ether, to give 13.69 g (70%) of tan needles, m.p. 52.5°-54°; infrared (melt) 3400 cm, 1600 (m), 1430 (m), 1325 (s); nmr ($CCl_4$) δ 8.64 (s, 1H) and δ 7.3-8.2 (m, 4H).

Anal. Calc'd. for $C_8H_5ClF_3NO$: C, 42.98; H, 2.25; Cl, 15.86; N, 6.26. Found: C, 42.98; H, 2.32; Cl, 16.13; N, 6.27.

Other hydroxamoyl chlorides prepared by this procedure were: benzohydroxamoyl chloride, m.p. 42°; p-chlorobenzohydroxamoyl chloride, m.p. 82°-84°; m-chlorobenzohydroxamoyl chloride, m.p. 61°-63°; m-nitrobenzohydroxamoyl chloride, m.p. 98°-101°.

EXAMPLE 74

Preparation of Ethyl 3-(α,α,α-Trifluoro-m-Tolyl)-4-Isoxazolecarboxylate. A solution of 4.87 g of ethyl β-pyrrolidinylacrylate (0.0288 mol) and 5.0 ml of triethylamine in 60 ml of ethyl ether was cooled to 0°. A solution of 6.43 g of m-trifluoromethylbenzohydroxamoyl chloride in 25 ml of ether was added over a period of 40 minutes with magnetic stirring, during which time a white precipitate of $Et_3N \cdot HCl$ formed. The mixture was stirred at 0° for 2.5 hours and filtered and the solid washed thoroughly with ether. The combined solutions were washed with 5% HCl and water, dried over $MgSO_4$, filtered and concentrated to 7.66 g of orange oil; only one peak was observed on GLC. Double distillation through a 4"×⅜" Vigreux column gave 5.95 g (72% crude), boiling point 98°-100° (0.08torr), slightly yellow oil, tlc (Silica Gel G, benzene) showed 3 spots, $R_f$ 0.21, 0.46, and 0.61. Chromatography of 5.80 g of the oil on 110 g of dry column silica gel (∼80 cm long) gave 1.79 g of oil (mixture $R_f$ 0.46 and 0.61, faint), first 120 ml benzene eluent and 3.78 g clear colorless oil in the second 120 ml benzene (pure by tlc, $R_f$ 0.46). The second fraction was distilled giving 2.85 g (34%) of pure product, boiling point 94° (0.045 torr), infrared (neat); 1720 cm$^{-1}$ (s), 1340 (s), 1120 (s); nmr ($CCl_4$) δ 1.25 (t, 3H), 4.26 (q, 2H), 7.4-8.2 (m, 4H) and 9.0 (s, 1H).

Anal. Calc'd. for $C_{13}H_{10}F_3NO_2$: C, 54.74; H, 3.53; F, 19.98; N, 4.91. Found: C, 54.68; H, 3.39; F, 19.87; N, 5.00.

EXAMPLE 75

Preparation of Ethyl 3-(4-Chlorophenyl)-4-Isoxazolecarboxylate. The crude product from the reaction of 4.23 g of ethyl β-pyrrolidinylacrylate (0.025 mol) and the nitrile oxide from 4.75 g p-chlorobenzohydroxamoyl chloride (0.025 mol) and 3.5 ml $Et_3N$ run as above, gave, after chromatography, 1.27 g (20%) of white solid, m.p. 43°-45°; infrared (melt); 1725 cm$^{-1}$ (s), 1290 (s) and 1170 (s); nmr ($CCl_4$) δ 1.35 (t, 3H), 4.30 (q, 2H), 7.4 and 7.8 (ABq, 4H) and 8.95 (s, 1H).

Anal. Calc'd. for $C_{12}H_{10}ClNO_3$: C, 57.27; H, 4.01; Cl, 14.09; N, 5.57. Found: C, 57.29; H, 3.88; Cl, 14.04; N, 5.35.

EXAMPLE 76

Preparation of Ethyl 3-(3-Chlorophenyl)-4-Isoxazolecarboxylate. The crude oil from the reaction of 4.23 g of ethyl β-pyrrolidinylacrylate (0.025 mol) and the nitrile oxide from 4.75 g of 3-chlorobenzohydroxamoyl chloride and 3.5 ml of $Et_3N$, run as in Example 74, was twice crystallized from petroleum ether to give 2.78 g (44%) of tan powder, m.p. 43°-45°; infrared (melt); 1720 cm$^{-1}$ (s), 1550 (s), 1290 (s), 1125 (s); nmr ($CCl_4$) δ 1.35 (t, 3H), 4.25 (q, 2H), 7.2-7.4 and 7.5-7.9 (complex, 4H), 8.95 (s, 1H).

Anal. Calc'd. for $C_{12}H_{10}ClNO_3$: C, 57.27; H, 4.01; Cl, 14.09; N, 5.57. Found: C, 57.07; H, 4.02; Cl, 13.99; N, 5.67.

EXAMPLE 77

Preparation of Ethyl 3-(3-Nitrophenyl)-4-Isoxazolecarboxylate. A mixture of 4.23 g (0.025 mol) of ethyl β-pyrrolidinylacrylate and 3.5 ml of triethylamine in 60 ml of anhydrous ether was cooled to −10°. A solution of 5.01 g (0.025 mol) of 3-nitrobenzohydroxamoyl chloride in 20 ml of ether was added dropwise in 30 minutes with rapid magnetic stirring. The mixture was stirred at −10°-0° for 4 hours and allowed to warm to room temperature overnight. The solid was removed by filtration and washed four times with 50 ml of boiling ether. The residues from the evaporation of the ether solutions were recrystallized from hexane and combined to give 3.72 g (58%) of white needles, m.p. 90°-92°; nmr (CCl$_4$) δ 1.30 (t, 3H), 4.27 (q, 2H), 7.47-8.80 (m, 4H) and 9.06 (s, 1H).

Anal. Calc'd. for $C_{12}H_{10}N_2O_5$: C, 54.97; H, 3.84; N, 10.68. Found: C, 55.07; H, 3.91; N, 10.59.

EXAMPLE 78

Preparation of Ethyl 3-(3-Cyanophenyl)-4-Isoxazolecarboxylate. A solution of 8.46 g (0.05 mol) of β-pyrrolidinylacrylate and 9.05 g (0.05 mol) of 3-cyanobenzohydroxamoyl chloride in 175 ml of ether was cooled to −15°. A solution of 7.0 ml of triethylamine in 15 ml of ether was added dropwise with magnetic stirring over 40 minutes. A dense white precipitate formed immediately. The mixture was stirred at 0° for 3 hours and allowed to warm to room temperature overnight. The dense suspension was thoroughly mixed with 400 ml of methylene chloride. The suspension was washed twice with water and twice with 6 N HCl. The aqueous solution was back-extracted with four 50-ml portions of methylene chloride. The combined organic solutions were washed with water and dried over anhydrous sodium sulfate, filtered, and concentrated to a nearly white solid. Recrystallization from benzene-hexane gave 9.57 g (79%) of slightly yellow needles, m.p. 135°-7°; infrared (KBr) 2245 cm$^{-1}$, nmr (CDCl$_3$) δ 1.37 (t, 3H), 4.40 (q, 2H), 7.6-8.3 (m, 4H) and 9.13 (s, 1H).

Anal. Calc'd. for $C_{13}H_{10}N_2O_3$: C, 64.46; H, 4.16; N, 11.56. Found: C, 64.49; H, 4.12; N, 11.56.

EXAMPLE 79

Preparation of Ethyl 3-Phenyl-4-Isoxazolecarboxylate. Utilizing the procedure of Example 78 with benzohydroxamoyl chloride as a reactant in lieu of 3-cyanobenzohydroxamoyl chloride, ethyl 3-phenyl-4-isoxazolecarboxylate was prepared as a crude oil.

Anal. Calc'd. for $C_{12}H_{11}NO_3$: C, 66.35; H, 5.10; N, 6.45. Found: C, 66.22; H, 5.09; N, 6.55.

Haloalkyl esters may be prepared from the free acid in accordance with Example 80.

EXAMPLE 80

Preparation of 2,2,2-Trifluoromethyl 3-(α,α,α-Trifluoro-m-Tolyl)-4-Isoxazolecarboxylate. A solution of 2.85 g ethyl ester prepared by Example 74 in 10 ml glacial acetic acid and 10 ml concentrated HCl was heated at reflux for 4 hours. The solution was cooled and most of the solvent removed by evaporation under reduced pressure. The pasty residue was washed with water and dried giving 2.2 g (85%) of acid, m.p. 115°-118°.

A solution of 5.31 g of the acid in 15 ml of thionyl chloride was heated at reflux for 1 hour. The excess thionyl chloride was removed by evaporation under reduced pressure giving 5.70 g of crude acid chloride (nmr showed no acid proton) which was used immediately in the following two reactions.

The crude acid chloride, 1.70 g, was stirred at room temperature with 5 ml of 2,2,2-trifluoroethanol for 1 hour and then heated at reflux for 2 hours. The excess alcohol was removed by evaporation to give a brown oil. The nmr spectrum showed two isoxazole ring protons indicating incomplete reaction. The mixture was dissolved in 5 ml 2,2,2-trifluoroethanol and heated at reflux for two hours and stirred at room temperature overnight. After removal of excess alcohol, the yield was 1.55 g of brown oil which was chromatographed on 25 g silica gel. Elution with 50 ml of 1:1 hexane-ether gave 1.51 g ester. Distillation gave 0.620 g pure ester, boiling point 88° 0.1 torr; nmr (CCl$_4$) δ 4.56 (q, 2H), 7.3-8.2 (m, 4H) and 9.05 (s, 1H).

Anal. Calc'd. for $C_{13}H_7F_6NO_3$: C, 46.03; H, 2.08; F, 33.61; N, 4.13. Found: C, 46.22; H, 2.03; F, 33.86; N, 4.28.

The isothiazolecarboxylates and the isoxazolecarboxylates of the present invention have been found to be effective in inhibiting the growth of undesirable plants. They are especially effective when applied to the soil before emergence of the undesirable plants. When tested in accordance with the procedures described below, some selectivity, i.e., reduction in herbicidal injury, was found with respect to narrowleaf crops such as wheat.

As used herein, the term "active ingredient" is understood to mean an isothiazolecarboxylate or isoxazolecarboxylate of the foregoing formula (I).

To illustrate the herbicidal properties of the compounds of the present invention, said compounds were tested in the following manner.

The pre-emergent test was conducted as follows.

A good grade of top soil was placed in aluminum pans and compacted to a depth of three-eighths to one-half inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil thoroughly mixed, and used as a cover layer for prepared pans. After treatment the pans were moved into a greenhouse bench where they were watered from below as needed to give adequate moisture for germination and growth.

Unless noted otherwise, approximately 4 weeks after seeding and treating, the plants were observed to determine all deviations from the normal growth habit and the results recorded. A herbicidal rating code was used to signify the extent of phytotoxicity of each species. The ratings are defined as follows:

| % Control | Rating |
| --- | --- |
| 0–24 | 0 |
| 25–49 | 1 |
| 50–74 | 2 |
| 75 100 | 3 |

The plant species utilized in these tests are identified by letter in accordance with the following legend:

A - Canada Thistle   K - Barnyard Grass
B - Cocklebur        L - Soybean
C - Velvetleaf       M - Sugar Beet
D - Morning Glory    N - Wheat
E - Lambsquarters    O - Rice
F - Smartweed        P - Sorghum
G - Nutsedge         Q - Wild Buckwheat
H - Quackgrass       R - Hemp Sesbania
I - Johnson Grass    S - Panicum Spp
J - Downy Brome      T - Crabgrass Results of the pre-emergent tests are summarized in Tables I and II, below.

TABLE I

| Compound of Example No. | Rate (kg/h) | A | B | C | D | E | F | G | H | I | J | K |
|---|---|---|---|---|---|---|---|---|---|---|---|---|
| 26 | 11.2 | 3 | 0 | 1 | 3 | 3 | — | 1 | 0 | 0 | 0 | 3 |
| 26 | 5.6 | 1 | 0 | 0 | 1 | 3 | — | 1 | 0 | 0 | 0 | 3 |
| 27 | 11.2 | 1 | 1 | 3 | 3 | 3 | — | 0 | 1 | 0 | 3 | 3 |
| 27 | 5.6 | 1 | 0 | 0 | 1 | 3 | — | 0 | 0 | 0 | 0 | 3 |
| 28 | 11.2 | 3 | 0 | 0 | 2 | 3 | — | 0 | 1 | 2 | 3 | 3 |
| 28 | 5.6 | 1 | 0 | 1 | 2 | 3 | — | 0 | 0 | 0 | 3 | 3 |
| 29 | 11.2 | 0 | 0 | 0 | 1 | 0 | 0 | 0 | 0 | 0 | 0 | 0 |
| 30 | 11.2 | 3 | 2 | 3 | 2 | 3 | — | 3 | 3 | 2 | 3 | 3 |
| 30 | 5.6 | 3 | 2 | 2 | 2 | 2 | — | 2 | 2 | 1 | 2 | 3 |
| 31 | 11.2 | 2 | 0 | 0 | 0 | 1 | — | 1 | 1 | 0 | 1 | 3 |
| 31 | 5.6 | 0 | 0 | 0 | 0 | 1 | — | 0 | 2 | 0 | 0 | 2 |
| 32 | 11.2 | 3 | 2 | 3 | 3 | 3 | 1 | 3 | 1 | 1 | 1 | 3 |
| 32 | 5.6 | 3 | 1 | 3 | 3 | 2 | 2 | 3 | 1 | 1 | 0 | 3 |
| 33 | 11.2 | 3 | 1 | 2 | 2 | 2 | 3 | 2 | 2 | 0 | 1 | 3 |
| 33 | 5.6 | 3 | 1 | 1 | 2 | 3 | 1 | 3 | 0 | 2 | 0 | 3 |
| 34 | 11.2 | 3 | 2 | 2 | 3 | 3 | 2 | 3 | 3 | 3 | 2 | 3 |
| 34 | 5.6 | 3 | 2 | 2 | 1 | 3 | 2 | 1 | 1 | 0 | 1 | 3 |
| 35 | 11.2 | 3 | 1 | 1 | 1 | 2 | 1 | 1 | 1 | 2 | 0 | 3 |
| 35 | 5.6 | 2 | — | 0 | 1 | 3 | 2 | 0 | 0 | 0 | 0 | 3 |
| 36 | 11.2 | 3 | 2 | 2 | 1 | 3 | 3 | 2 | 1 | 0 | 1 | 3 |
| 36 | 5.6 | 3 | 1 | 1 | 1 | 1 | 0 | 1 | 1 | 0 | 0 | 3 |
| 37 | 11.2 | 3 | 3 | 2 | 2 | 3 | 2 | 3 | 2 | 1 | 1 | 3 |
| 37 | 5.6 | 3 | 2 | 0 | 1 | 3 | 2 | 2 | 2 | 3 | 1 | 3 |
| 38 | 11.2 | 3 | — | 2 | 2 | 3 | 3 | 2 | 1 | 3 | 2 | 3 |
| 38 | 5.6 | 2 | — | 3 | 2 | 3 | 3 | 2 | 3 | 3 | 1 | 3 |
| 39* | 11.2 | 1 | 1 | 0 | 0 | 2 | 2 | 0 | 0 | 0 | 0 | 1 |
| 39* | 5.6 | 1 | 0 | 0 | 0 | 0 | 1 | 0 | 0 | 1 | 0 | 0 |
| 40 | 11.2 | 3 | — | 2 | 3 | 3 | — | 3 | 3 | 3 | 3 | 3 |
| 40 | 5.6 | 3 | — | 1 | 3 | 3 | — | 3 | 3 | 3 | 1 | 3 |
| 41 | 11.2 | 3 | 2 | 2 | 3 | 3 | — | 3 | 3 | 3 | 2 | 3 |
| 41 | 5.6 | 3 | 2 | 1 | 2 | 2 | — | 3 | 2 | 3 | 1 | 3 |
| 42 | 11.2 | 3 | 3 | 2 | 2 | 2 | — | 3 | 3 | 1 | 2 | 3 |
| 42 | 5.6 | 3 | 1 | 0 | 2 | 1 | — | 3 | 1 | 1 | 0 | 3 |
| 43 | 11.2 | 3 | 2 | 1 | 2 | 1 | — | 1 | 0 | 3 | 0 | 3 |
| 43 | 5.6 | 2 | 0 | 1 | 1 | 1 | — | 0 | 0 | 0 | 0 | 3 |
| 44 | 5.6 | 3 | 2 | 2 | 2 | 2 | 3 | 1 | 0 | 0 | 1 | 3 |
| 45 | 11.2 | 0 | 0 | 0 | 1 | 1 | 0 | 0 | 0 | 0 | 0 | 1 |
| 45 | 5.6 | 1 | 1 | 0 | 1 | 0 | 0 | 0 | 0 | 0 | 0 | 1 |
| 51 | 5.6 | 2 | 0 | 0 | 1 | 1 | 3 | 0 | 2 | 2 | 0 | 2 |
| 53 | 11.2 | 3 | 1 | 0 | 1 | 2 | 1 | 3 | 1 | 0 | 0 | 3 |
| 53 | 5.6 | 2 | 1 | 1 | 0 | 3 | 0 | 3 | 0 | 0 | 0 | 3 |
| 55 | 11.2 | 3 | 3 | 3 | 3 | 3 | 2 | 2 | 2 | 0 | 3 | 3 |
| 55 | 5.6 | 3 | 1 | 1 | 3 | 1 | 1 | 1 | 0 | 0 | 0 | 2 |
| 56 | 5.6 | 3 | 0 | 1 | 2 | 2 | 3 | 2 | 3 | 3 | 0 | 3 |
| 57 | 11.2 | 1 | 0 | 0 | 1 | 0 | — | 0 | 0 | — | 0 | 0 |
| 58 | 5.6 | 3 | 0 | 0 | 3 | 0 | — | 0 | 1 | 0 | 0 | 2 |
| 59 | 5.6 | 1 | 0 | 0 | 1 | 0 | 0 | 0 | 0 | 0 | 0 | 0 |
| 64 | 11.2 | 2 | — | 1 | 3 | 3 | — | 0 | 1 | 0 | 0 | 3 |
| 65 | 11.2 | 1 | — | 0 | 1 | 0 | — | 0 | 0 | 0 | 0 | 0 |
| 66 | 11.2 | 3 | 2 | 3 | 3 | 3 | 1 | 3 | 1 | 3 | 0 | 3 |
| 66 | 5.6 | 3 | 1 | 1 | 2 | 1 | 1 | 1 | 0 | 3 | 0 | 3 |
| 67 | 11.2 | 3 | 2 | 1 | 3 | 2 | 3 | 2 | 1 | 3 | 0 | 3 |
| 67 | 5.6 | 3 | 1 | 1 | 2 | 2 | 1 | 2 | 1 | 2 | 0 | 3 |
| 68 | 11.2 | 3 | 2 | 1 | 2 | 2 | — | 1 | 0 | 0 | 0 | 3 |
| 68 | 5.6 | 3 | 2 | 2 | 1 | 3 | — | 3 | 1 | 2 | 0 | 3 |
| 69 | 11.2 | 2 | — | 1 | 2 | 3 | — | 0 | 0 | 0 | 1 | 1 |
| 70* | 11.2 | 0 | — | 0 | 0 | 0 | 0 | 0 | 0 | 0 | 0 | 0 |
| 70* | 5.6 | 0 | 0 | 0 | 0 | 0 | 0 | 0 | 0 | 0 | 0 | 0 |
| 71* | 11.2 | 0 | 0 | 0 | 0 | 0 | 0 | 3 | 0 | 0 | 0 | 1 |
| 71* | 5.6 | 1 | 0 | 0 | 0 | 0 | 0 | 0 | 0 | 0 | 0 | 0 |
| 71* | 5.6 | 3 | 0 | 0 | 1 | 3 | 3 | 1 | 0 | 0 | 0 | 0 |
| 74 | 11.2 | 3 | 3 | 1 | 3 | 3 | 2 | 2 | 3 | 3 | 3 | 3 |
| 74 | 5.6 | 3 | 2 | 1 | 1 | 2 | 0 | 1 | 3 | 3 | 3 | 3 |
| 75 | 11.2 | 3 | 0 | 0 | 1 | 1 | 1 | 0 | 1 | 0 | 0 | 1 |
| 75* | 5.6 | 1 | 0 | 0 | 0 | 0 | 0 | 0 | 3 | 0 | 0 | 1 |
| 76 | 11.2 | 3 | 0 | 2 | 3 | 3 | 3 | 0 | 1 | 0 | 0 | 3 |
| 76 | 5.6 | 2 | 0 | 0 | 1 | 3 | 0 | 0 | 3 | 0 | 0 | 3 |
| 77* | 11.2 | 0 | 0 | 0 | 3 | 0 | 0 | 0 | 0 | 0 | 0 | 0 |
| 77* | 5.6 | 0 | 3 | 0 | 0 | 0 | 0 | 0 | 0 | 0 | 0 | 0 |
| 78 | 11.2 | 2 | 1 | 1 | 1 | 1 | 0 | 0 | 0 | 0 | 0 | 0 |
| 78* | 5.6 | 1 | 0 | 1 | 1 | 0 | 0 | 0 | 0 | 0 | 0 | 0 |
| 80 | 11.2 | 3 | 2 | 2 | 3 | 1 | 2 | 1 | 3 | 0 | 3 | 3 |
| 80 | 5.6 | 3 | 0 | 1 | 0 | 0 | 0 | 1 | 3 | 0 | 2 | 1 |

*plants observed 2 weeks after treatment.

TABLE II

| Compound of Ex. Number | Rate (kg/h) | L | M | N | O | P | B | Q | D | R | E | F | C | J | S | K | T |
|---|---|---|---|---|---|---|---|---|---|---|---|---|---|---|---|---|---|
| 26 | 5.6 | 0 | 2 | 1 | 0 | 0 | 0 | 0 | 1 | 1 | 0 | — | 0 | 0 | 0 | 3 | 3 |
| 26 | 1.12 | 0 | 0 | 0 | 0 | 0 | 1 | 0 | 1 | 0 | 0 | — | 0 | 0 | 0 | 0 | 0 |
| 27 | 11.2 | 0 | 3 | 1 | 0 | 1 | 0 | 0 | 2 | 3 | 3 | 3 | 1 | 2 | 1 | 3 | 3 |
| 27 | 8.4 | 0 | 2 | 0 | 0 | 0 | 0 | 0 | 2 | 1 | 3 | 1 | 1 | 0 | 1 | 3 | 3 |
| 27 | 5.6 | 0 | 3 | 1 | 1 | 1 | 0 | 1 | 2 | 2 | 2 | — | 2 | 1 | 3 | 3 | 3 |
| 27 | 1.12 | 0 | 0 | 0 | 1 | 0 | 0 | 0 | 0 | 0 | 0 | — | 0 | 0 | 0 | 0 | 1 |
| 28 | 5.6 | 0 | 2 | 0 | 0 | 0 | 0 | 0 | 1 | 2 | 2 | — | 1 | 0 | 2 | 3 | 3 |
| 28 | 1.12 | 0 | 0 | 0 | 0 | 0 | 0 | 0 | 0 | 0 | 0 | — | 0 | 0 | 1 | 1 | 3 |
| 28* | 0.28 | 0 | 0 | 0 | 0 | 0 | 0 | 0 | 0 | 0 | 0 | — | 0 | 1 | 0 | 0 | 1 |
| 30 | 5.6 | 3 | 3 | 1 | 3 | 3 | 2 | 3 | 2 | 3 | 2 | — | 2 | 2 | 3 | 3 | 2 |
| 30 | 1.12 | 1 | 3 | 0 | 3 | 2 | 1 | 1 | 2 | 2 | 2 | — | 2 | 0 | 2 | 3 | 1 |
| 30 | 0.28 | 0 | 2 | 0 | 0 | 0 | 1 | 0 | 2 | 0 | 1 | — | 0 | 0 | 2 | 1 | 0 |
| 31* | 5.6 | 1 | 2 | 2 | 2 | 3 | 1 | 0 | 3 | 1 | 1 | — | 1 | 2 | 3 | 3 | 3 |
| 31* | 1.12 | 0 | 0 | 0 | 0 | 0 | 0 | 0 | 0 | 0 | 0 | — | 0 | 0 | 0 | 1 | 0 |
| 32 | 5.6 | 2 | 3 | 0 | 2 | 3 | 2 | 3 | 3 | 3 | 3 | 3 | 3 | 2 | 3 | 3 | 3 |
| 32 | 1.12 | 1 | 2 | 0 | 1 | 3 | 1 | 0 | 3 | 2 | 2 | 1 | 1 | 0 | 2 | 3 | 1 |
| 32 | 0.25 | 0 | 2 | 0 | 0 | 0 | 1 | 0 | 0 | 0 | 0 | 0 | 0 | 0 | 0 | 1 | 1 |
| 33 | 5.6 | 0 | 2 | 0 | 1 | 3 | 1 | 2 | 2 | 1 | 1 | 1 | 2 | 1 | 1 | 3 | 1 |
| 33* | 1.12 | 0 | 0 | 0 | 0 | 0 | 0 | 0 | 1 | 0 | 0 | 0 | 0 | 0 | 0 | 0 | 0 |
| 34 | 5.6 | 3 | 3 | 0 | 3 | 3 | 1 | 3 | 2 | 2 | 3 | 2 | 1 | 1 | 3 | 3 | 3 |
| 34* | 1.12 | 0 | 0 | 0 | 0 | 0 | 0 | 0 | 0 | 0 | 0 | 0 | 0 | 0 | 1 | 2 | 1 |
| 35 | 5.6 | 2 | 1 | 0 | 1 | 3 | — | 0 | 1 | 1 | 0 | 0 | 1 | 0 | 2 | 3 | 2 |
| 35** | 1.12 | 0 | 1 | 0 | 0 | 0 | — | 0 | 0 | 0 | 0 | 0 | 0 | 0 | 0 | 0 | 0 |
| 36 | 5.6 | 1 | 2 | 0 | 1 | 2 | 0 | 2 | 1 | 1 | 2 | 1 | 1 | 1 | 2 | 3 | 3 |

TABLE II-continued

| Compound of Ex. Number | Rate (kg/h) | L | M | N | O | P | B | Q | D | R | E | F | C | J | S | K | T |
|---|---|---|---|---|---|---|---|---|---|---|---|---|---|---|---|---|---|
| 36* | 1.12 | 0 | 1 | 0 | 0 | 0 | 0 | 0 | 0 | 0 | 0 | 0 | 1 | 0 | 1 | 2 | 0 |
| 37 | 5.6 | 1 | 2 | 0 | 1 | 3 | — | 1 | 2 | 1 | 2 | 1 | 0 | 1 | 3 | 3 | 3 |
| 37 | 11.2 | 1 | 1 | 0 | 0 | 0 | — | 1 | 0 | 3 | 2 | 1 | 0 | 0 | 0 | 1 | 0 |
| 37* | 0.28 | 2 | 0 | 0 | 0 | 0 | 0 | 0 | 0 | 0 | 1 | 0 | 0 | 0 | 0 | 0 | 0 |
| 38 | 5.6 | 3 | 3 | 0 | 3 | 3 | — | 1 | 3 | 2 | 2 | 2 | 1 | 0 | 2 | 3 | 3 |
| 38 | 1.12 | 1 | 2 | 0 | 0 | 0 | — | 0 | 3 | 0 | 0 | 0 | 1 | 0 | 0 | 3 | 1 |
| 38* | 0.28 | 0 | 1 | 0 | 0 | 0 | — | 0 | 1 | 0 | 0 | 0 | 0 | 0 | 0 | 0 | 0 |
| 40 | 5.6 | 2 | 2 | 1 | 3 | 3 | 2 | 3 | 3 | 3 | 2 | — | 1 | 2 | 3 | 3 | 3 |
| 40 | 1.12 | 1 | 1 | 0 | 1 | 3 | 1 | 1 | 1 | 2 | 1 | — | 0 | 1 | 3 | 3 | 2 |
| 41 | 5.6 | 2 | 3 | 1 | 2 | 3 | 2 | 2 | 2 | 3 | 2 | — | 1 | 1 | 3 | 3 | 3 |
| 41 | 1.12 | 0 | 1 | 0 | 1 | 2 | 2 | 1 | 1 | 1 | 2 | — | 0 | 0 | 3 | 3 | 1 |
| 42 | 5.6 | 0 | 2 | 0 | 1 | 3 | 1 | 2 | 2 | 1 | 2 | — | 1 | 1 | 3 | 3 | 1 |
| 42 | 1.12 | 0 | 1 | 0 | 0 | 0 | 0 | 0 | 0 | 0 | 0 | — | 0 | 0 | 0 | 3 | 1 |
| 43 | 5.6 | 0 | 2 | 1 | 2 | 2 | 1 | 0 | 1 | 1 | 3 | — | 2 | 0 | 1 | 3 | 1 |
| 43 | 1.12 | 0 | 1 | 0 | 0 | 0 | 0 | 0 | 0 | 0 | 0 | — | 0 | 0 | 0 | 0 | 0 |
| 44* | 1.12 | 1 | 1 | 0 | 0 | 0 | 0 | 0 | 0 | 0 | 1 | 0 | 0 | 0 | 0 | 3 | 0 |
| 51 | 1.12 | 0 | 0 | 0 | 0 | 0 | 0 | 0 | 0 | 0 | 0 | 0 | 0 | 0 | 0 | 0 | 0 |
| 51* | 0.28 | 0 | 1 | 0 | 0 | 0 | 0 | 0 | 0 | 0 | 0 | 0 | 0 | 0 | 0 | 0 | 0 |
| 53 | 5.6 | 2 | 3 | 0 | 1 | 3 | 2 | 1 | 2 | 2 | 2 | 0 | 0 | 0 | 3 | 3 | 1 |
| 53 | 1.12 | 1 | 2 | 0 | 1 | 0 | 0 | 0 | 1 | 1 | 1 | 0 | 0 | 0 | 1 | 3 | 0 |
| 55 | 5.6 | 3 | 2 | 0 | 0 | 2 | 2 | 0 | 3 | 2 | 2 | 1 | 1 | 0 | 0 | 3 | 3 |
| 55 | 1.12 | 1 | 1 | 0 | 0 | 0 | 1 | 1 | 1 | 3 | 1 | 1 | 0 | 0 | 0 | 0 | 0 |
| 56 | 1.12 | 1 | 2 | 1 | 0 | 2 | 3 | 0 | 2 | 1 | 1 | 1 | 1 | 1 | 2 | 3 | 1 |
| 56 | 0.56 | 0 | 2 | 0 | 0 | 2 | 0 | 0 | 0 | 0 | 1 | — | 0 | 0 | 1 | 3 | 0 |
| 58* | 1.12 | 0 | 0 | 0 | 0 | 0 | 0 | 0 | 0 | 0 | 0 | 0 | 0 | 0 | 0 | 0 | 0 |
| 64 | 5.6 | 1 | 2 | 1 | 1 | 2 | 1 | 0 | 2 | 1 | 2 | — | 1 | 0 | 0 | 3 | 2 |
| 64 | 1.12 | 0 | 1 | 0 | 0 | 0 | 0 | 0 | 0 | 0 | 1 | — | 0 | 0 | 0 | 3 | 0 |
| 66 | 5.6 | 1 | 3 | 0 | 2 | 3 | 2 | 2 | 2 | 3 | 2 | 2 | 2 | 0 | 3 | 3 | 0 |
| 66 | 1.12 | 1 | 2 | 0 | 0 | 0 | 1 | 0 | 0 | 1 | 0 | 0 | 1 | 0 | 0 | 0 | 0 |
| 67 | 5.6 | 1 | 2 | 0 | 0 | 3 | 1 | 2 | 3 | 2 | 2 | 1 | 1 | 1 | 3 | 3 | 1 |
| 67* | 1.12 | 0 | 1 | 0 | 0 | 0 | 0 | 0 | 0 | 0 | 0 | 0 | 0 | 0 | 0 | 1 | 0 |
| 68 | 1.12 | 0 | 2 | 1 | 1 | 3 | 1 | 2 | 3 | 1 | 3 | — | 1 | 0 | 1 | 2 | 1 |
| 69* | 5.6 | 0 | 0 | 0 | 0 | 0 | 0 | 0 | 0 | 0 | 0 | — | 0 | 0 | 0 | 0 | 0 |
| 74 | 5.6 | 2 | 3 | 3 | 3 | 3 | 1 | 3 | 1 | 3 | 1 | 2 | 2 | 3 | 3 | 3 | 3 |
| 74 | 1.12 | 1 | 1 | 1 | 1 | 1 | 0 | 0 | 0 | 2 | 0 | 0 | 1 | 3 | 1 | 1 | 2 |
| 76 | 5.6 | 2 | 2 | 0 | 1 | 0 | 0 | 0 | 1 | 3 | 2 | 0 | 1 | 0 | 0 | 3 | 0 |
| 80 | 5.6 | 1 | 1 | 1 | 3 | 2 | 1 | 0 | 1 | 3 | 0 | 0 | 2 | 3 | 3 | 3 | 1 |
| 80 | 1.12 | 0 | 0 | 0 | 1 | 0 | — | 0 | 0 | 0 | 0 | 0 | 0 | 0 | 0 | 0 | 0 |

*plants observed 2 weeks after treatment.
**Plants observed 3 weeks after treatment.

The post-emergent tests were conducted as follows.

The active ingredients are applied in spray form to two or three-week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately four weeks later the effects are observed and recorded. The results are shown in Tables III and IV in which the post-emergent herbicidal rating code is as follows:

| % Control | Rating |
|---|---|
| 0-24 | 0 |
| 25-49 | 1 |
| 50-74 | 2 |
| 75-99 | 3 |
| 100 | 4 |

The plant species utilized in these tests are identified by letter in accordance with the previous legend.

TABLE III

| Compound of Example No. | Rate (kg/h) | A | B | C | D | E | F | G | H | I | J | K |
|---|---|---|---|---|---|---|---|---|---|---|---|---|
| 26* | 11.2 | 0 | 0 | 0 | 0 | 0 | — | 0 | 0 | 0 | 0 | 0 |
| 27* | 11.2 | 2 | 1 | 1 | 0 | 0 | — | 0 | 0 | 0 | 0 | 0 |
| 28 | 11.2 | 2 | 1 | 1 | 1 | 0 | — | 0 | 0 | 0 | 0 | 0 |
| 29* | 11.2 | 0 | 0 | 0 | 0 | 0 | 0 | 0 | 0 | 0 | 0 | 0 |
| 30 | 11.2 | 1 | 1 | 1 | 1 | 1 | — | 0 | 0 | 0 | 0 | 0 |
| 31 | 11.2 | 1 | 1 | 1 | 1 | 1 | — | 1 | 0 | 0 | 0 | 0 |
| 32 | 11.2 | 2 | 2 | 2 | 2 | 1 | 0 | 0 | 0 | 0 | 0 | 0 |
| 33 | 11.2 | 3 | 2 | 2 | 3 | 2 | 2 | 1 | 1 | 0 | 0 | 0 |
| 33 | 4.48 | 2 | 2 | 2 | 3 | 2 | 1 | 0 | 1 | 0 | 0 | 0 |
| 34 | 11.2 | 2 | 2 | 2 | 2 | 1 | 1 | 0 | 0 | 1 | 0 | 0 |
| 35 | 11.2 | 1 | 2 | 1 | 3 | 2 | 1 | 1 | 1 | 1 | 0 | 1 |
| 36 | 11.2 | 2 | 2 | 1 | 2 | 2 | 1 | 1 | 0 | 0 | 0 | 1 |
| 37* | 11.2 | 2 | 1 | 1 | 2 | 3 | 0 | 0 | 0 | 0 | 0 | 0 |
| 37* | 4.48 | 1 | 1 | 0 | 1 | 3 | 0 | 0 | 0 | 0 | 0 | 0 |
| 38 | 11.2 | 2 | 2 | 2 | 3 | 2 | 2 | 1 | 1 | 0 | 0 | 2 |
| 39* | 11.2 | 0 | 1 | 0 | 1 | 3 | 0 | — | 0 | 0 | 0 | 0 |
| 40 | 11.2 | 3 | — | 1 | 2 | 1 | — | 1 | 1 | 0 | 0 | 0 |
| 40 | 4.48 | 2 | 1 | — | 2 | 2 | — | 1 | 0 | 2 | 3 | 1 |
| 41 | 11.2 | 2 | 2 | 1 | 3 | 1 | — | 0 | 0 | 0 | 0 | 0 |
| 42 | 11.2 | 2 | 2 | 1 | 2 | 1 | — | 1 | 1 | 0 | 0 | 2 |
| 43 | 11.2 | 2 | 2 | 2 | 2 | 2 | — | 1 | 0 | 0 | 0 | 0 |
| 44 | 11.2 | 1 | 1 | 1 | 1 | 0 | — | 0 | 0 | 0 | 0 | 0 |
| 45* | 11.2 | 0 | 0 | 0 | 0 | 0 | 0 | 0 | 0 | 0 | 0 | 0 |
| 51* | 4.48 | 0 | 0 | 0 | 0 | 2 | 0 | — | 0 | 0 | 0 | 0 |
| 53* | 11.2 | 1 | 0 | 0 | 1 | 1 | 0 | 0 | 0 | 0 | 0 | 0 |
| 55 | 11.2 | 0 | 0 | 0 | 1 | 1 | 0 | 0 | 0 | 0 | 0 | 0 |
| 56 | 4.48 | 1 | 1 | 1 | 1 | 2 | 1 | 0 | 0 | 0 | 0 | 0 |
| 57* | 11.2 | 0 | 0 | 0 | 0 | 0 | — | 0 | 0 | 0 | 0 | 0 |
| 58 | 11.2 | 0 | 0 | 0 | 0 | 0 | 0 | 0 | 0 | 0 | 0 | 0 |
| 59* | 4.48 | 0 | 0 | 0 | 0 | 0 | — | 0 | 0 | 0 | 0 | 0 |
| 64* | 11.2 | 0 | — | 0 | 0 | 0 | — | 0 | 0 | 0 | 0 | 0 |

TABLE III-continued

| Compound of Example No. | Rate (kg/h) | A | B | C | D | E | F | G | H | I | J | K |
|---|---|---|---|---|---|---|---|---|---|---|---|---|
| 65 | 11.2 | 1 | — | 0 | 2 | 2 | — | 0 | 0 | 0 | 0 | 0 |
| 66 | 11.2 | 3 | 2 | 2 | 3 | 1 | 0 | 0 | 0 | 0 | 0 | 0 |
| 66 | 4.48 | 1 | 2 | 1 | 2 | 1 | 0 | 0 | 0 | 0 | 0 | 0 |
| 67 | 11.2 | 2 | 2 | 2 | 2 | 1 | — | 0 | 0 | 0 | 0 | 0 |
| 68 | 11.2 | — | 2 | 2 | 2 | 1 | — | 0 | 0 | 0 | 0 | 2 |
| 68 | 4.48 | 4 | 2 | 2 | 2 | 1 | — | 1 | 0 | — | 0 | 0 |
| 69 | 11.2 | 1 | — | 0 | 1 | 1 | — | 0 | 0 | 0 | 0 | 0 |
| 70* | 11.2 | — | 0 | 1 | 1 | 3 | 0 | 0 | 0 | 0 | 0 | 0 |
| 70* | 4.48 | 0 | 1 | 0 | 1 | 1 | 0 | 0 | 0 | 0 | 0 | 0 |
| 71* | 11.2 | 0 | — | 0 | 1 | 4 | 0 | 0 | 0 | 0 | 0 | 0 |
| 74 | 11.2 | 2 | 1 | 1 | 1 | 1 | — | 0 | 0 | 0 | 0 | 0 |
| 75* | 11.2 | — | 0 | 0 | 1 | 0 | 0 | 0 | 0 | 0 | 0 | 0 |
| 76 | 11.2 | 2 | 1 | 1 | 1 | 1 | — | 0 | 0 | 1 | 0 | 0 |
| 77 | 11.2 | 0 | 1 | 0 | 1 | 0 | 0 | 0 | 0 | 0 | 0 | 0 |
| 78 | 11.2 | 0 | 1 | 0 | 2 | 1 | 0 | 0 | 0 | 0 | 0 | 0 |
| 80 | 11.2 | 2 | 2 | 2 | 3 | 1 | 0 | 0 | 0 | 0 | 0 | 1 |

*plants observed 2 weeks after treatment.

TABLE IV

| Compound of Ex. Number | Rate (kg/h) | L | M | N | O | P | B | Q | D | R | E | F | C | J | S | K | T |
|---|---|---|---|---|---|---|---|---|---|---|---|---|---|---|---|---|---|
| 33 | 1.12 | 1 | 1 | 0 | 0 | 0 | 2 | 1 | 2 | 0 | 0 | 0 | 1 | 0 | 0 | 0 | 0 |
| 33 | 4.48 | 1 | 1 | 1 | 0 | 0 | 2 | 2 | 3 | 1 | 2 | 1 | 2 | 0 | 0 | 0 | 0 |
| 35* | 1.12 | 1 | 1 | 0 | 0 | 0 | — | 1 | 3 | 1 | 0 | 0 | 0 | 0 | 0 | 1 | 0 |
| 35* | 4.48 | 1 | 1 | 0 | 0 | 1 | 1 | 1 | 3 | 2 | 3 | 1 | 1 | 0 | 0 | 1 | 0 |
| 38* | 1.12 | 1 | 0 | 0 | 0 | 0 | — | 1 | 3 | 1 | 1 | 0 | 1 | 0 | 0 | 0 | 0 |
| 38* | 4.48 | 1 | 1 | 0 | 0 | 1 | 1 | 1 | 3 | 3 | 1 | 1 | 1 | 0 | 1 | 1 | 0 |
| 41 | 1.12 | 1 | 1 | 0 | 0 | 0 | 1 | 1 | 1 | 1 | 2 | — | 1 | 0 | 0 | 0 | 0 |
| 41 | 4.48 | 1 | 1 | 1 | 0 | 2 | 1 | 1 | 1 | 1 | 2 | — | 2 | 0 | 0 | 1 | 1 |
| 66 | 1.12 | 0 | 0 | 0 | 0 | 0 | 2 | 2 | 2 | 2 | 4 | 0 | 1 | 0 | 0 | 0 | 0 |
| 80* | 4.48 | 1 | 0 | 0 | 0 | 1 | — | 3 | 3 | 2 | 2 | 1 | 2 | 0 | 1 | 1 | 1 |
| 80 | 4.48 | 1 | 0 | 0 | 1 | 1 | — | 2 | 2 | 3 | 2 | 1 | 2 | 0 | 3 | 1 | 0 |

*plants observed 2 weeks after treatment.

and Y is either hydrogen or trifluoromethyl. Most preferred are those isothiazolecarboxylates in which X is trifluoromethyl in the 3-position.

The herbicidal activity of the isothiazole and isoxazole carboxylates of formula (I) is somewhat unexpected in view of the relatively weak herbicidal activity of corresponding isothiazolecarboxylic acid compounds, some of which are known compounds. Tables V and VI, below, summarize the results obtained when such isothiazolecarboxylic acids were tested in accordance with the heretofore described procedures. All observations were recorded 14 days after treatment. Table V summarizes the results of the pre-emergent test. Table VI summarizes the results of the post-emergent test.

When operating in accordance with the present invention, effective amounts of the active ingredients are

TABLE V

| Compound | Rate (kg/h) | A | B | C | D | E | F | G | H | I | J | K |
|---|---|---|---|---|---|---|---|---|---|---|---|---|
| 3-(p-chlorophenyl)-4-isothiazolecarboxylic acid | 5.6 | 0 | 0 | 0 | 0 | 0 | — | 0 | 0 | 0 | 0 | 0 |
| 3-t-butyl-4-isothiazolecarboxylic acid | 5.6 | 0 | 0 | 0 | 0 | 0 | 0 | 0 | 0 | 0 | 0 | 0 |
| 3-phenyl-4-isothiazolecarboxylic acid | 5.6 | — | 0 | 0 | 1 | 2 | — | 0 | 3 | 0 | 0 | 1 |
| 3-(2,6-dichlorophenyl)-isothiazolecarboxylic acid | 11.2 | 0 | 0 | 0 | 0 | 0 | — | 0 | 0 | 0 | 0 | 0 |

TABLE VI

| Compound | Rate (kg/h) | A | B | C | D | E | F | G | H | I | J | K |
|---|---|---|---|---|---|---|---|---|---|---|---|---|
| 3-(p-chlorophenyl)-4-isothiazolecarboxylic acid | 4.48 | 0 | 0 | 1 | 0 | 0 | — | 0 | 0 | 0 | 0 | 0 |
| 3-t-butyl-4-isothiazolecarboxylic acid | 4.48 | 0 | 0 | 0 | 0 | 0 | 0 | 0 | 0 | 0 | 0 | 0 |
| 3-phenyl-4-isothiazolecarboxylic acid | 4.48 | 2 | 0 | 1 | 2 | 0 | — | 0 | 0 | 0 | 0 | 0 |
| 3-(2,6-dichlorophenyl)-isothiazolecarboxylic acid | 11.2 | 1 | 0 | — | 0 | 0 | — | 0 | 0 | 0 | 0 | 0 |

The above tables illustrate that the isothiazolecarboxylates and isoxazolecarboxylates of the foregoing formula (I) are effective in inhibiting the growth of undesirable plants. Especially preferred are those compounds in which X is trifluoromethyl in the 3-position applied to the plant system. By application to the plant system is meant the application of the active ingredient in or on soil or plant growth media and/or applied above-ground portions of plants in any convenient fashion.

Application to the soil or growth media can be carried out by simply mixing with soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above-ground portions of plants can be carried out by conventional methods, e.g. power dusters, boom and hand sprayers and spray dusters. The formulations can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

Tables I, II, III and IV indicate that the active ingredient is more effective when applied to the soil as a preemergent, i.e., before the weeds emerge from the soil, and this type of treatment is, therefore, preferred.

In selecting the appropriate time and rate of application of the active ingredient, it will be recognized that precise rates will also be dependent upon the desired response, mode of application, plant variety, soil conditions and various other factors known to those skilled in the art. While a rate of about 1.00 to 11.2 kilos per hectare is preferred, rates of from 0.05 to about 56 kilos per hectare may be used, depending upon the factors noted above. In addition, it will be recognized that single or multiple applications may be used to exert the desired response.

The active ingredient can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Compositions of this invention generally contain from about 1 to 99 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of inhibiting the growth of undesirable plants which comprises applying to the plant system a herbicidally effective amount of a compound having the formula

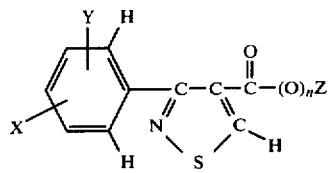

wherein X and Y are independently selected from the group consisting of hydrogen, lower alkyl, lower alkoxy, trifluoromethyl, halogen, cyano and nitro; n is zero or one provided that when n is zero, Z is selected from the group consisting of chloro and $NR_1R_2$ wherein $R_1$ and $R_2$ are independently selected from the group consisting of hydrogen and lower alkyl; when n is one, Z is selected from the group consisting of alkyl having up to 12 carbon atoms inclusive, alkyl having up to 5 carbon atoms inclusive which have been substituted with from 1 to 3 halogen atoms, inclusive, benzyl, lower alkoxy lower alkyl, allyl, monochlorinated allyl, dichlorinated allyl,

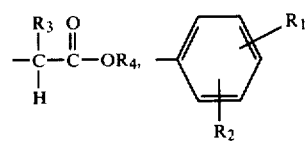

and agriculturally acceptable cations; wherein $R_1$ and $R_2$ are as previously defined, $R_3$ is hydrogen or methyl and $R_4$ is lower alkyl.

2. A method according to claim 1 wherein Z is alkyl having up to 12 carbon atoms inclusive.

3. A method according to claim 1 wherein X is trifluoromethyl and Y is hydrogen or trifluoromethyl.

4. A method according to claim 3 wherein X is in the 3-position.

5. A method according to claim 4 wherein Y is hydrogen.

6. A method according to claim 1 wherein said compound has the formula

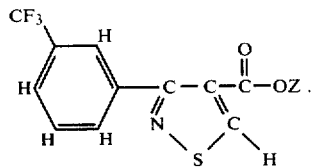

7. A method according to claim 1 which comprises applying said compound to the soil before the emergence of the undesirable plants.

* * * * *